(12) United States Patent
Almasri et al.

(10) Patent No.: US 10,274,492 B2
(45) Date of Patent: Apr. 30, 2019

(54) HIGH SENSITIVITY IMPEDANCE SENSOR

(71) Applicant: The Curators of the University of Missouri, Columbia, MO (US)

(72) Inventors: Mahmoud Almasri, Columbia, MO (US); Shibajyoti Ghosh Dastider, Columbia, MO (US); Shuping Zhang, Columbia, MO (US); Majed El Dweik, Jefferson City, MO (US); Nuh Sadi Yuksek, Columbia, MO (US); Ibrahem Jasim, Columbia, MO (US); Jiayu Liu, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 15/094,045

(22) Filed: Apr. 8, 2016

(65) Prior Publication Data

US 2016/0299138 A1    Oct. 13, 2016

Related U.S. Application Data

(60) Provisional application No. 62/145,842, filed on Apr. 10, 2015.

(51) Int. Cl.
*G01N 33/569* (2006.01)
*B03C 5/00* (2006.01)
(Continued)

(52) U.S. Cl.
CPC .. *G01N 33/56916* (2013.01); *B01L 3/502761* (2013.01); *B03C 5/005* (2013.01);
(Continued)

(58) Field of Classification Search
CPC ......... G01N 33/56916; G01N 33/5438; G01N 27/06; B03C 5/005; B03C 5/026; B01L 3/502761; B01L 3/502707
See application file for complete search history.

(56) References Cited

U.S. PATENT DOCUMENTS 5,653,859 A * 8/1997 Parton ..................... B03C 5/028
204/450
7,169,282 B2    1/2007 Talary et al.
(Continued)

FOREIGN PATENT DOCUMENTS

WO    2010007350 A1    1/2010

OTHER PUBLICATIONS

Dastider et al., MEMS biosensor for detection of *Escherichia coli* O157:H7 in food products, year:2011, UMI 1521070, Proquest, pp. 1-73.*
(Continued)

*Primary Examiner* — Melanie Brown
(74) *Attorney, Agent, or Firm* — Thompson Coburn LLP

(57) ABSTRACT

Disclosed herein are example embodiments of a transformative sensor apparatus that is capable of detecting and quantifying the presence of a substance of interest such as a specified bacteria within a sample via changes in impedance exhibited by a detection electrode array. In an example embodiment, sensitivity is improved by including a focusing electrode array in a rampdown channel to focus a concentration of the substance of interest into a detection region. The focusing electrodes include an opposing pair of electrodes in a rampdown orientation. The focusing electrode may also include tilted thin film finger electrodes extending from the rampdown electrodes. In another example embodi-
(Continued)

ment, trapping electrodes are positioned to trap a concentration of the substance of interest onto the detection electrode array.

38 Claims, 39 Drawing Sheets

(51) Int. Cl.
  *G01N 33/543* (2006.01)
  *B01L 3/00* (2006.01)
  *B03C 5/02* (2006.01)
  *G01N 27/06* (2006.01)

(52) U.S. Cl.
  CPC ......... *B03C 5/026* (2013.01); *G01N 33/5438* (2013.01); *B01L 3/502707* (2013.01); *B01L 2200/0647* (2013.01); *B01L 2300/0645* (2013.01); *B01L 2300/087* (2013.01); *B01L 2300/0816* (2013.01); *B01L 2300/0864* (2013.01); *B01L 2300/0867* (2013.01); *B01L 2300/0887* (2013.01); *B01L 2400/0424* (2013.01); *B03C 2201/26* (2013.01); *G01N 27/06* (2013.01); *G01N 2333/245* (2013.01); *G01N 2333/255* (2013.01)

(56) References Cited

U.S. PATENT DOCUMENTS

| | | | |
|---|---|---|---|
| 7,635,420 B1 | 12/2009 | Li et al. | |
| 7,686,934 B2 | 3/2010 | Hodko et al. | |
| 7,704,362 B2 | 4/2010 | Hamers et al. | |
| 7,811,439 B1 | 10/2010 | Simmons et al. | |
| 8,257,571 B1 | 9/2012 | Cummings et al. | |
| 8,524,063 B2 | 9/2013 | Hughes et al. | |
| 2001/0053535 A1* | 12/2001 | Bashir | G01N 33/5438 435/34 |
| 2008/0105565 A1* | 5/2008 | Davalos | B03C 5/005 205/775 |
| 2008/0283402 A1* | 11/2008 | Peach | B01L 3/502761 204/547 |
| 2009/0008254 A1* | 1/2009 | Muller | B03C 5/005 204/547 |
| 2010/0193361 A1* | 8/2010 | Enjoji | B03C 5/026 204/643 |
| 2011/0192726 A1* | 8/2011 | Chen | A61B 5/14546 204/547 |

OTHER PUBLICATIONS

Dastider et al., A micromachined impedance biosensor for accurate and rapid detection of *E. coli* O157:H7, RSC Advances, 2013; 26297-26306.

Dastider et al., Impedance Biosensor Based on Interdigitated Electrode Arrays for Detection of Low Levels of *E. coli* O157;H7, IEEE, Jan. 20-24, 2013, pp. 955-958.

Hamada et al, "A rapid bacteria detection technique utilizing impedance measurement combined with positive and negative dielectrophoresis", Sensors and Actuators B 181 (2013) 439-445.

* cited by examiner

Cr / Au is sputtered on a SU-8 2005 coated glass substrate.

2.

Au is patterned on a SU-8 2005 to create the interdigitated electrode arrays, traces, bonding pads, and seed layer for electroplating the focusing electrode.

| SU-8 2005 (802) | Chromium (804) | Gold (806) | SU-8 2025 (808) |
| PDMS (812) | Fluidic connector (814) | | |
| Glass (800) | | | |
| AZ 4620 (810) | | | |

4.

Au is electroplated to create vertical side side wall electrode.

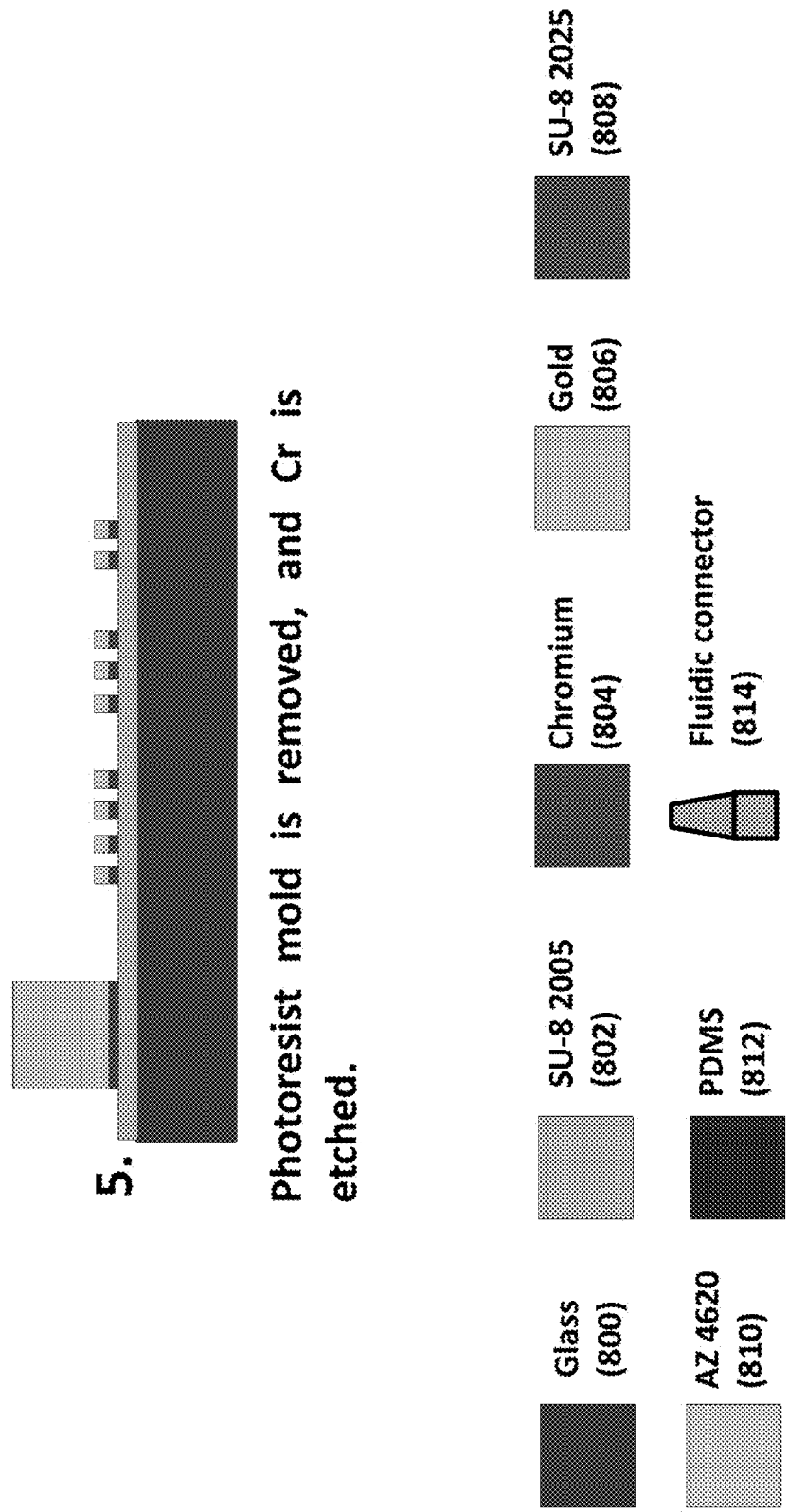

SU-8 2025 is spincoated and patterned to create microfluidic channel.

A PDMS cover with inlet-outlet holes is cured and bonded to the microchannel layer using $O_2$ plasma technique.

Fabrication

- Glass
- SU-8 2025
- Connector
- SU-8 2005
- Au
- AZ 4620
- PDMS
- Cr

Step 1: Physical Vapor Deposition of Cr / Au on SU-8 2005 layer

← Sputtered thin film Au surface

Device Fabrication

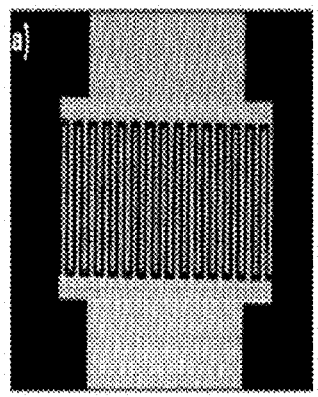
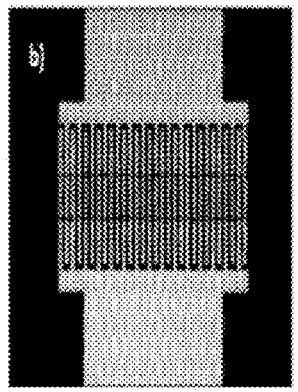

a) Patterned bottom interdigitated electrode array, b) patterned photoresist sacrificial microchannel across the interdigitated electrode fingers

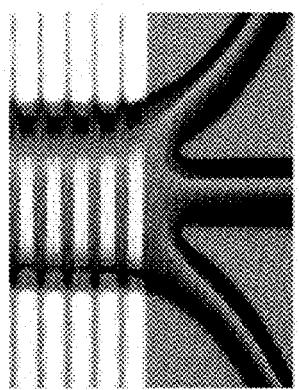

Optical image and SEM micrograph of the photoresist sacrificial channel on the interdigitated electrode array

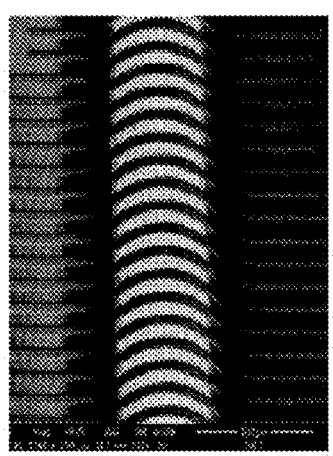
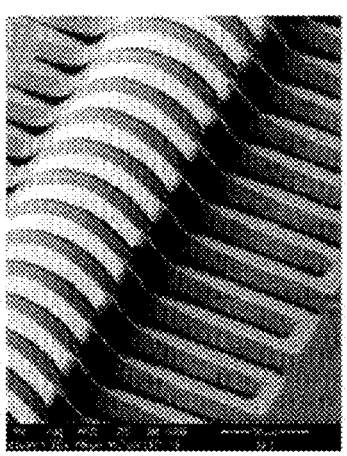

SEM micrograph of the of the patterned interdigitated electrode fingers on top of the sacrificial microchannel

Figure 11B

HIGH SENSITIVITY IMPEDANCE SENSOR

CROSS-REFERENCE AND PRIORITY CLAIM TO RELATED APPLICATION

This patent application claims priority to U.S. provisional patent application Ser. No. 62/145,842, filed Apr. 10, 2015, the entire disclosure of which is incorporated herein by reference.

STATEMENT REGARDING FEDERALLY SPONSORED RESEARCH OR DEVELOPMENT

This invention was made with government support under Contract No. 0022929 awarded by the National Science Foundation and Contract Nos. 0020735 and 0040951 awarded by the United States Department of Agriculture. The government has certain rights in the invention.

INTRODUCTION

Food-borne disease outbreaks can spread quickly and impact large populations within a very short period of time. In the United States alone, disease outbreaks due to consumption of contaminated food causes an estimated 48 million illnesses, including 128,000 hospitalizations and 3000 deaths in 2011. These outbreaks have significant impact on health and the economy.

The pathogenic strain of *Escherichia coli* O157:H7 ("*E. coli* O157:H7") is the most common source for widespread food-borne disease outbreak. *E. coli* O157:H7 produces a harmful Shiga toxin that affects intestines, resulting in symptoms that may cause anemia, stomach cramps and diarrhea. Quick detection of this bacterium in food samples is important for containing outbreaks. However, prior detection techniques have suffered from slowness and low sensitivity.

In an effort to improve upon these shortcomings in the art, the inventors disclose a number of embodiments of a transformative sensor apparatus that is capable of detecting and quantifying the presence of bacteria of interest within a sample via changes in impedance exhibited by a detection electrode array.

In an example embodiment, sensitivity is improved by including a focusing electrode array in a rampdown channel upstream from a detection region of the sensor apparatus to focus a concentration of the bacteria of interest into the detection region. The focusing electrodes may include an opposing pair of electrodes in a rampdown orientation. The focusing electrode may also include tilted thin film finger electrodes extending from the rampdown electrodes. By applying an alternating voltage at a specified frequency to the focusing electrode array, the bacteria of interest can be concentrated toward a desired portion of the focusing region via dielectrophoresis. The concentrated flow of bacteria can then be passed into the detection region for detection.

In another example embodiment, trapping electrodes are positioned to trap a concentration of the bacteria of interest onto the detection electrode array. By applying an alternating voltage at a specified frequency to the trapping electrodes, the bacteria of interest can be concentrated onto a detection electrode array via dielectrophoresis.

In still another example embodiment, the focusing electrode array and trapping electrodes can be combined in the sensor apparatus to further improve sensitivity. For example, an example embodiment of such a sensor apparatus that employs the focusing electrode array in combination with the trapping electrodes can be capable of detecting the presence of *E. coli* O157:H7 cells within a sample at concentrations in a range between around 5 CFU/ml to around $10^4$ CFU/mL.

Further still, for other embodiments, substances other than bacteria can be detected via the inventive sensor technology. For example, the substances for detection can be any substance that will contribute to an impedance change by the detection electrodes. By way of example, such substances may include any antigens or substances that elicit antibody responses, including but not limited to viruses, viral antigens, fungal antigens, toxins, toxic substances, antibiotic residues. The substances could also be used to detect antibodies against any antigens or substances.

These and other features and advantages of the present invention will be apparent to those having ordinary skill in the art upon review of the teachings in the following description and drawings.

BRIEF DESCRIPTION OF THE DRAWINGS

FIGS. 8A-G depict a side view of an example fabrication process for a biosensor apparatus in accordance with an example embodiment.

FIG. 11B depicts an example electrode fabrication process for a biosensor apparatus in accordance with the example embodiments of FIGS. 10A and 10B.

DETAILED DESCRIPTION OF EXAMPLE EMBODIMENTS

Figure 1:
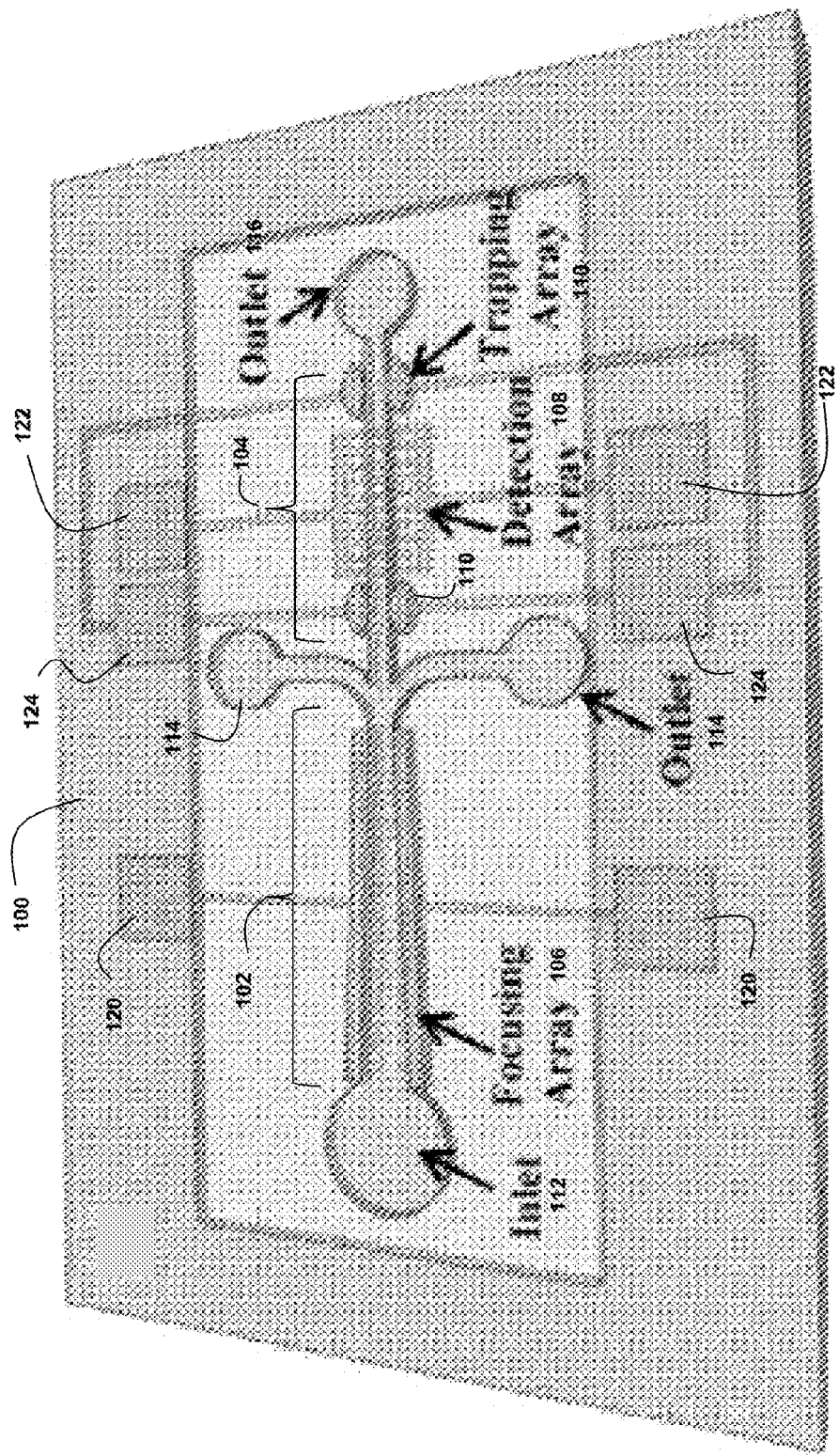
FIG. 1 depicts an example embodiment of a biosensor apparatus.

FIG. 1 depicts an example embodiment of a biosensor apparatus 100 that is capable of sensing the presence of particles of interest such as bacteria within a fluid material. The apparatus 100 includes a channel through which the fluid material flows from an inlet 112 to an outlet 116. This channel may take the form of a microchannel. The channel includes a focusing region 102 and a detection region 104 along a flow path for the fluid material. The detection region 104 is positioned downstream from the focusing region 102 with respect to the flow direction of the flow path.

While the example of FIG. 1 and other examples disclosed below are described as biosensors that detect the presence of bacteria in fluid samples, it should be understood (as explained above) that substances other than bacteria or other biological substances can be detected via such sensor technology. Accordingly, it should be understood that the sensor technology of FIG. 1 and other figures disclosed herein is labeled as a biosensor by way of example, and other embodiments of the sensor technology disclosed herein can detect non-biological substances that would produce an impedance change in the detection electrode array.

Furthermore, in many of the example embodiments discussed below, the bacteria of interest is *E. coli* 0157:H7. However, it should be understood that the inventive technology disclosed herein can also be used to detect other bacteria of interest. For example, the bacteria of interest may also be *E. coli* O26, or *E. coli* O111. As another example, the inventive technology disclosed herein can be used to detect a plurality of bacteria of the family Enterobacteriaceae. Accordingly, the bacteria of for detection may comprise a bacteria selected from the group consisting of *Escherichia, Klebsiella, Proteus, Enterobacter, Aerobacter, Serratia, Providencia, Citrobacter, Morganella, Yersinia, Envinia, Shigella, Salmonella*, and combinations thereof. As yet another example, the bacteria for detection may comprise a plurality of *Bacillus, Campylobacter, Listeria, Staphylococcus, Streptococcus*, or *Vibrio* bacteria. Furthermore, the samples being tested can include fluid material corresponding to food products. Examples of such food products include peanut butter, cantaloupes, mangoes, tomatoes, and others.

The focusing region 102 includes a focusing electrode array 106 that is configured to create a concentration of the bacteria within the fluid material so that the concentrated mass of bacteria can be directed into the detection region 104. Through this technique, the concentration of bacteria within the fluid material exiting the focusing region 102 and entering the detection region 104 will be higher than the concentration of bacteria within the fluid material entering the focusing region 102 from inlet 112. Thus, the focusing region facilitates detection of the bacteria within the fluid material in situations where there may be a low concentration of bacteria present.

In the example of FIG. 1, the focusing electrode array 106 focuses the bacteria concentration toward a center portion of the channel, which has the effect of directing the bulk fluid material toward the waste outlets 114 that are disposed along an outer portion of the channel. The detection region 104 receives the bacteria-concentrated flow of fluid material from the center portion of the focusing region 102.

Figure 2A:
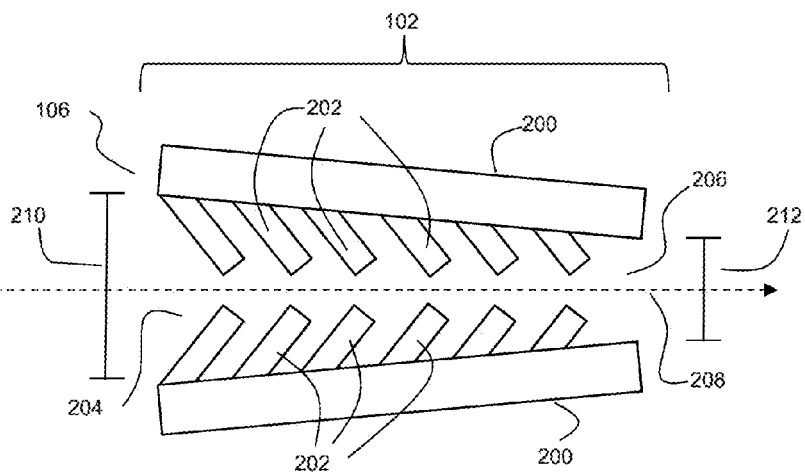
FIGS. 2A-2C provide various views of example embodiments of a focusing electrode array.
Figure 2B:
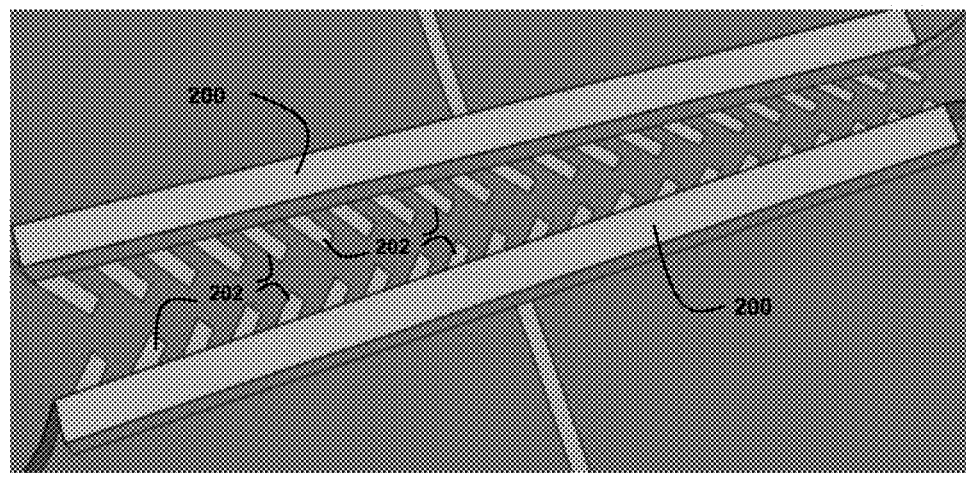
Figure 2C:
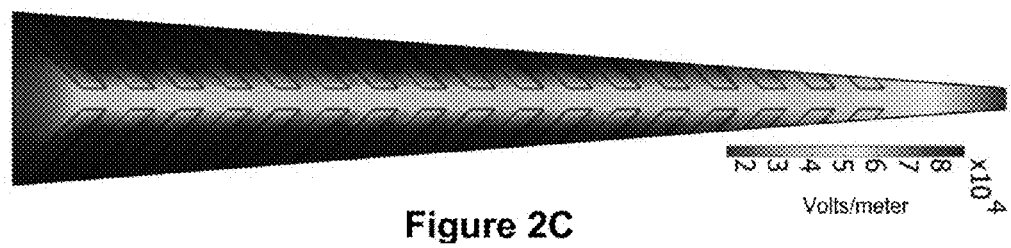

In the example of FIG. 1, the focusing region 102 is arranged as a rampdown channel. As used herein, the term "rampdown" in combination with channel refers to an arrangement where the channel is wider at its inlet than its outlet and progressively narrows along the length of the channel. For example, the rampdown channel can have dimensions such as a length of around 3 mm, a width at entrance 204 of around 300 µm, a width at exit 206 of around 100 µm, and a height of around 15 µm. As shown by FIGS. 2A-2C, the focusing electrode array 106 may include a pair of opposing vertical electrodes 200 that are arranged in a rampdown orientation to define the rampdown channel of the focusing region 102. As shown by FIGS. 2A-2C, the distance 210 between the opposing vertical electrodes 200 is greater at the entrance 204 to the flow path than the distance 212 between opposing vertical electrodes 200 at the exit 206 from the flow path. The electrodes 200 shown by FIGS. 2A and 2B are characterized as "vertical" with respect to a reference system where the horizontal dimension is the "floor" of the rampdown channel and the electrodes 200 are the "walls". However, it should be understood that the characterization of which of the dimensions are "horizontal" and "vertical" is arbitrary.

In an example embodiment, the distance 210 between electrodes 200 at the rampdown channel inlet 204 can be 80 µm while the distance 212 between electrodes 210 at the rampdown channel outlet 206 can be 10 µm. However, it should be understood that other rampdown widths and ratios could be employed. Furthermore, an example length of the focusing region 102 can be a length within the range of 2-4 mm. Once again, it should be understood that other lengths could be used.

The electrodes 200 provide focusing effects on the bacteria within the fluid material via dielectrophoresis (DEP). In the example of FIGS. 2A-2C, the electrodes 200 are configured to provide positive-DEP (p-DEP) forces via a non-uniform electric field created by applying an alternating voltage at a specified frequency to the electrodes 200. For example, this voltage signal can exhibit a voltage that falls in a range between around 4-10 Vp-p and a frequency that falls in a range between around 1-10 MHz. This voltage can be applied to the electrodes 200 via the contacts/bonding pads 120 shown by FIG. 1.

The p-DEP and hydrodynamic forces arising from the rampdown orientation of electrodes 200 operate to push the bacteria toward the center of the rampdown channel (e.g., see center line 208) and direct this concentration of bacteria in the central portion of the rampdown channel toward the detection region 104 (see the arrow of center line 208). The bulk fluid material will keep flowing toward the outer portion of the rampdown channel and into waste outlets 114 shown by FIG. 1. Thus, the fluid material entering the detection region 104 will have a higher concentration of bacteria than the fluid material entering the focusing region 102 due to the focusing effects created by the electrodes 200 in the rampdown orientation.

As shown by FIGS. 2A-2C, the focusing electrode array 106 also includes thin film finger pair electrodes 202 extending outward from the vertical wall of each electrode 200. In the example of FIGS. 2A-2C, the finger electrodes 202 are orthogonal to the electrodes 200. Thus, in this example, finger electrodes 202 are in a horizontal dimension while electrodes 200 are in a vertical dimension (such that finger electrodes 202 effectively form part of the floor of the rampdown channel while electrodes 200 form part of the walls). Moreover, the finger electrodes 202 are in a tilted orientation such that opposing finger pair electrodes are not perpendicular to the center line 208 that defines a longitudinal axis of the rampdown channel. In an example embodiment, these tilted thin film finger pair electrodes 202 are at a 45 degree angle relative to the center line 208. However, it should be understood that other tilt angles could be used.

Thus, for the focusing electrode array 106 shown by FIGS. 2A-2C, initially the tilted thin film finger pair electrodes 202 will generate the larger p-DEP forces that dominate the focusing process as the alternated voltage is applied to the electrodes 200 and 202 at the specified frequency. This will focus the bacteria in a narrow line in the center region of the rampdown channel (e.g., around 8-10 μm wide). As the channel ramps down, the generated p-DEP force from the electrode pairs 200 becomes more dominant relative to the finger electrode pairs 202 to dominate the focusing process and push the bacteria of interest in the central portion of the channel toward the detection region 104 (see FIG. 2C which shows a simulation of the electric field produced within the rampdown channel by the electrodes 200 and 202 in an example embodiment).

In an example embodiment, (1) the width of each finger electrode 202 can be around 10 μm, (2) the spacing between each adjacent finger electrode 202 extending outward from the same electrode 200 can be around 10 μm, and (3) the spacing between the distal ends of opposing pairs of finger electrodes 202 can be around 8 μm (where the distal ends are the ends of the finger electrodes 202 that are opposite the proximal ends that contact the electrodes 200). However, it should be understood that other values could be employed. Furthermore, an example focusing electrode array can include 100-200 pairs of finger electrodes 202, although more or fewer finger electrodes 202 can be employed if desired by a practitioner. It should be understood that the dimensions and orientations of the finger electrodes 202 as well as the dimensions and orientations of the electrodes 200 in concert with the applied voltage characteristics can be varied by practitioners to achieve a desired focusing effect for a given application.

The detection region 104 includes a detection electrode array 108, with the detection region being bookended by a trapping electrode array 110. As the concentrated mass of bacteria flows into the detection region, the detection electrode array 108 will exhibit a change in impedance as a function of the bacteria concentration. This impedance change can then be measured by an impedance analyzer circuit that is connected to the detection electrode array 108 via contacts/bonding pads 122 to determine and quantify a presence of bacteria in the fluid material. In an example embodiment, the impedance analyzer circuit may take the form of an Agilent impedance analyzer, although it should be understood that other techniques for measuring impedance could be used. Thus, an impedance transduction mechanism can be used to detect and quantify bacteria by measuring the electrical properties (impedance change) of the bacteria of interest (e.g., *E. coli*) caused by binding target molecules (e.g., *E. coli*) to the receptors (antibodies) immobilized on the surface of the detection electrode array 108 (discussed below). The magnitude and phase of the impedance across the detection electrode array 108 can be measured as a function of frequency using an impedance analyzer for various concentrations in order to determine the lowest measurable concentration. The testing of each sample concentration will be performed multiple times (e.g., six times) in order to obtain statistically viable data. A modulated AC voltage (sine wave) can be applied to the detection electrode array 108 at a frequency in a range of 10 Hz.-10 MHz. The impedance will be measured prior to immobilizing the antibodies on to the surface of the detection electrode array 108, after immobilizing the antibodies, and after the exposure of bacteria. A practitioner can use this technique to determine the impedance of the bacteria effect alone. In addition, the effect of frequency on impedance measurement can be monitored and analyzed. This technique can establish the baseline impedance and enable the extraction of the impedance due to the bacteria of interest alone.

Figure 3A:
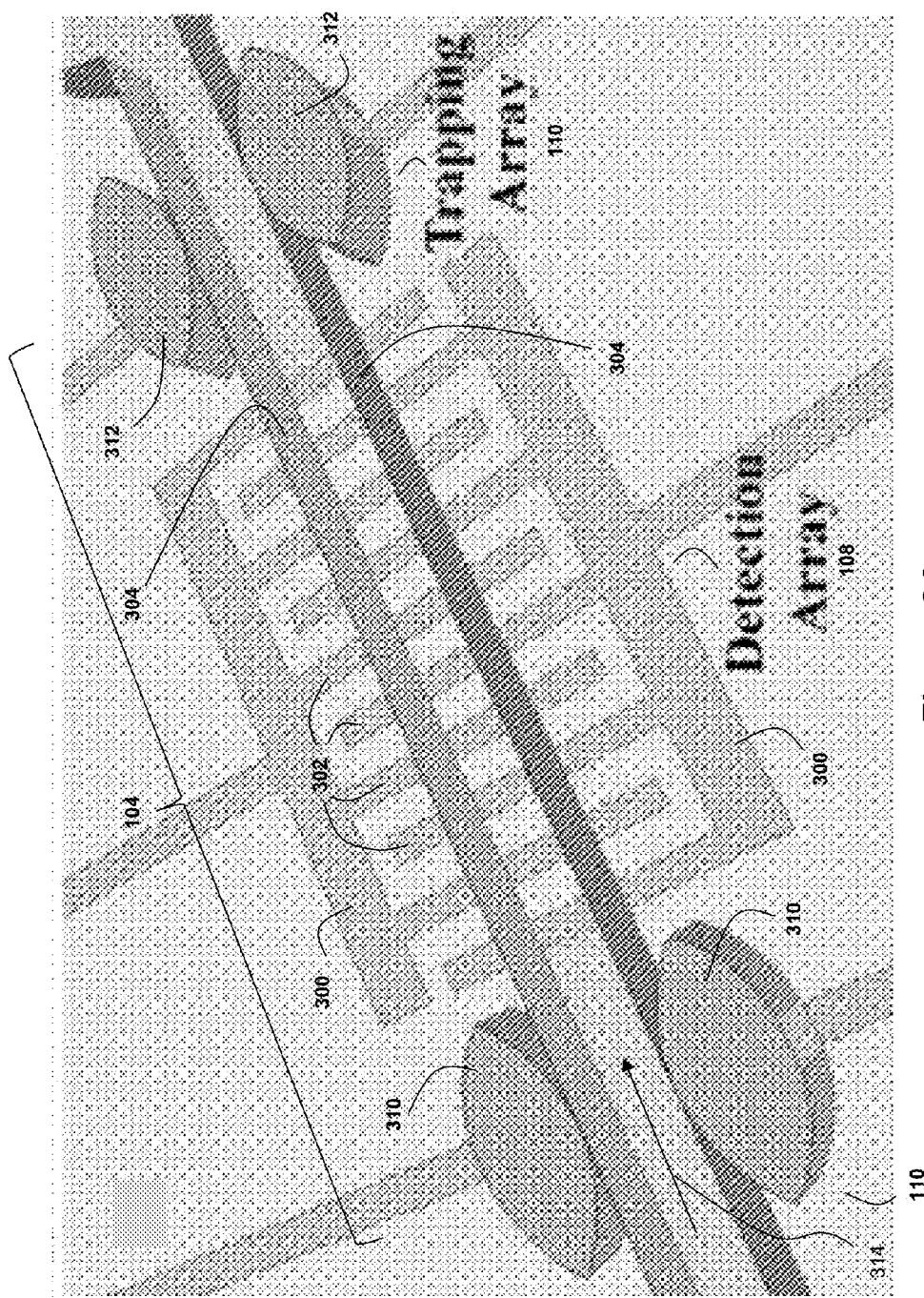
FIG. 3A depicts an example embodiment of a detection electrode array in combination with trapping electrode arrays.
Figures 3B, 3C:
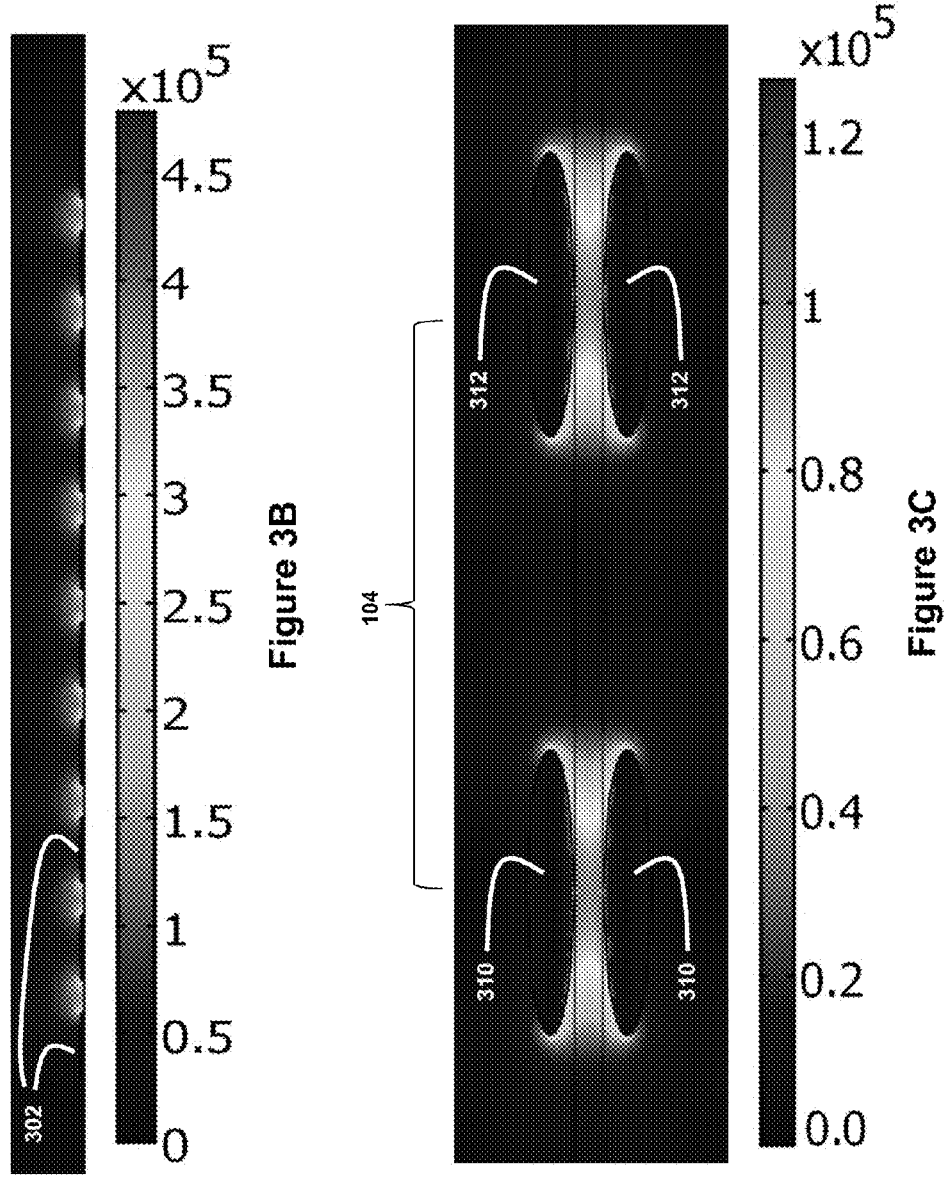
FIG. 3B depicts electric field gradients produced by an example set of detection electrodes.
FIG. 3C depicts electric field gradients produced by an example set of trapping electrodes.

FIG. 3A shows an example embodiment of the detection region 104. The detection electrode array 108 may take the form of an interdigitated electrode (IDE) array in a horizontal orientation (e.g., along the floor of the channel). The IDE array may comprise opposing pairs of electrodes 300 and finger electrodes 302 connected horizontally 300. The IDE electrode array 300 is disposed longitudinally along the length of the channel with the fingers 302 connected laterally across the width of the channel. An example IDE array may comprise 25 pairs of finger electrodes 302, although it should be understood that more or fewer finger electrodes 302 can be included in the IDE array. Also, in an example embodiment, each finger electrode may have a length of around 30 μm and a width in a range of around 5-10 μm, although a practitioner may choose to employ different lengths and/or widths. The spacing between the opposing interdigitated finger electrodes 302 can be in a range between around 2-10 μm, although once again a practitioner may choose different spacing amounts. For example, based on modeling results, it is expected that miniaturization of the IDE array will significantly increase the impedance measurement sensitivity, with the spacing between the opposing interdigitated finger electrodes having greater influence on the strength of E-field intensity compared with the width of the fingers. FIG. 3B shows a plot of E-field simulation for the IDE array when an alternating voltage at a specified frequency is applied across the IDE array. For example, this voltage signal can exhibit a voltage that falls in a range between around 4-10 Vp-p and a frequency that falls in a range between around 1-10 MHz.

To promote a binding of the bacteria of interest to the detection electrode array 108, a bacteria-specific antibody can be introduced into the detection region 104. The antibody will coat the surface of the finger electrodes 302 within the channel, and the bacteria of interest will bind with the antibody on the finger electrodes 302 to cause the impedance change that is indicative of the concentration of the bacteria of interest within the detection region 104. In an example embodiment where the bacteria of interest is *E. coli* 0157: H7, the antibody can be specific to *E. coli* 0157:H7. In embodiments where other antigens are used, the antibody can be specific to those antigens in order to promote attachment. For example, the antibodies can be introduced into the detection region 104, and once the detection region 104 is filled with the media, the flow can be stopped for 15-20 minutes, during which time the antibody will adsorb nonspecifically to the surface of the detection electrode array 108 (e.g., a gold surface of the detection electrode array 108 in an example embodiment). Any unbounded antibodies can be washed using DI water. Next, the corresponding bacteria of interest can flow through the detection region, and the bacteria of interest will bind to the antibody on the detection electrode array 108 due to the specificity of the capture antibody for that bacteria of interest.

To further enhance the sensitivity of the biosensor, the trapping electrode array 110 is employed to more greatly concentrate the bacteria of interest onto the detection electrode array 108. As shown by FIG. 3A, the trapping electrode array 110 may comprise a first pair of opposing vertical electrodes 310 that are positioned in the detection region 104 upstream from the detection electrode array 108 (with reference to the flow direction 314 of fluid material entering the detection region 104 of the channel defined by channel walls 304) and a second pair of opposing vertical electrodes 312 that are positioned in the detection region 104 downstream from the detection electrode array 108 (with reference to the flow direction 314).

The trapping electrodes 310 and 312 provide trapping effects on the bacteria within the fluid material via negative DEP (n-DEP). In the example of FIG. 3A, the electrodes 310 and 312 are configured to produce the n-DEP forces via a non-uniform electric field created by applying an alternating voltage at a specified frequency across the trapping electrode pairs 310 and 312. For example, this voltage signal can exhibit a voltage that falls in a range between around 4-10 Vp-p and a frequency that falls in a range between around 1-10 MHz. This voltage can be applied to the electrodes 310 and 312 via the contacts/bonding pads 124 shown by FIG. 1. The trapping electrodes 310 and 312 thus generate a high E-field gradient that forces the bacteria of interest away from the trapping electrodes 310 and 312 and toward the portion of the channel with a relatively lower E-field gradient. Given the positioning of the detection electrode array 108 between the trapping electrodes 310 and 312, this will significantly increase the chance of placing the bacteria of interest on top of the detection electrode array 108.

Figure 3D:
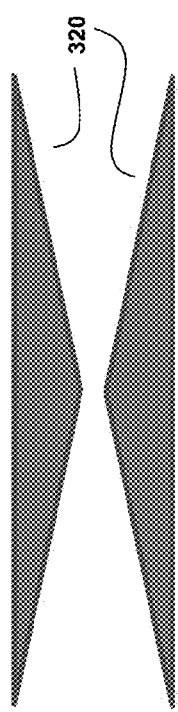
FIG. 3D depicts another example embodiment for a trapping electrode array.

The electrodes 310 and 312 can be designed to exhibit an elliptical shape as shown by the example of FIGS. 3A and 3C. In an example embodiment, the elliptical electrodes 310 and 312 can also exhibit a length of 100 μm and a height of 10 μm, although it should be understood that different lengths and/or widths could be used. As shown by the simulation plot of FIG. 3C, the non-uniform electric field gradient is highest in the channel region that is between the closest parts of the opposing electrode pairs, and the gradient decreases as the distance between opposing electrode pairs increases and as one moves along the length of the channel away from the opposing electrode pairs. The voltage applied at a specific frequency to the trapping electrodes 310 and 312 polarizes the bacteria of interest (e.g., E. coli cells (or any dielectric particles)) such that they will exhibit n-DEP behavior. Thus, they will be forced to move away from the vicinity of the trapping electrodes 310 and 312 toward the detection electrode array 108 and be trapped there. It is noted that the use of vertical electrodes for the trapping electrodes 310 and 312 also results in a non-uniform E-field gradient across the height of the electrodes 310 and 312 and thus further improving cell trapping mechanism. Furthermore, it should be understood that a practitioner can further adjust or optimize the trapping characteristics of electrodes 310 and 312 through changes to the shape and/or dimensions of the electrodes 310 and 312 as well as changes to the voltage and frequency of the signal applied to electrodes 310 and 312. For example, any shape that will cause the electrodes 310 and 312 to generate a non-uniform electric field may be used (see, for example, FIG. 3D which shows an example embodiment where the trapping electrodes 320 exhibit a triangular shape such that the apex of each opposing triangular electrode 320 is closest to the microchannel while the base of each opposing triangular electrode 320 is farthest from the microchannel).

Figure 3E:
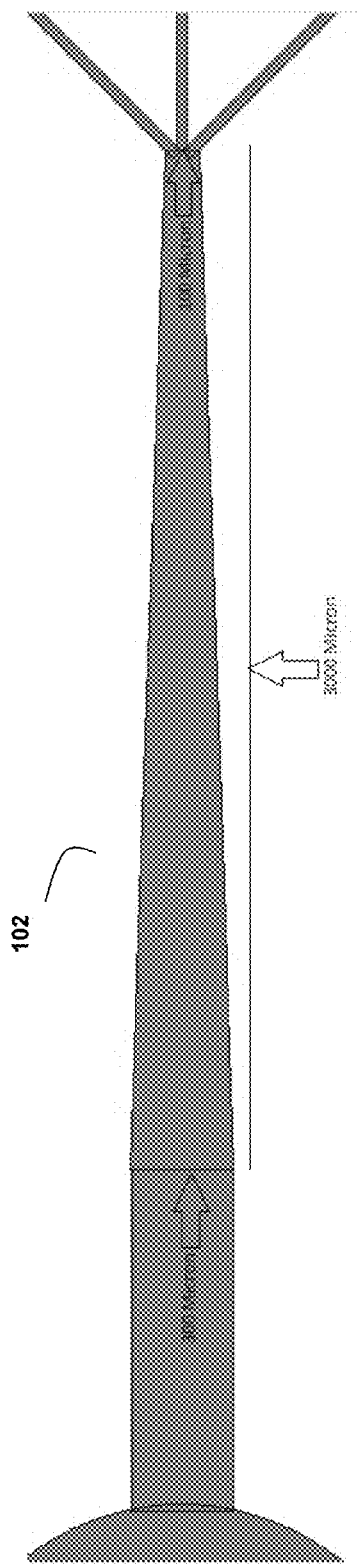
FIGS. 3E-3G depict example dimensions for example embodiments of the sensor apparatus.
Figure 3F:
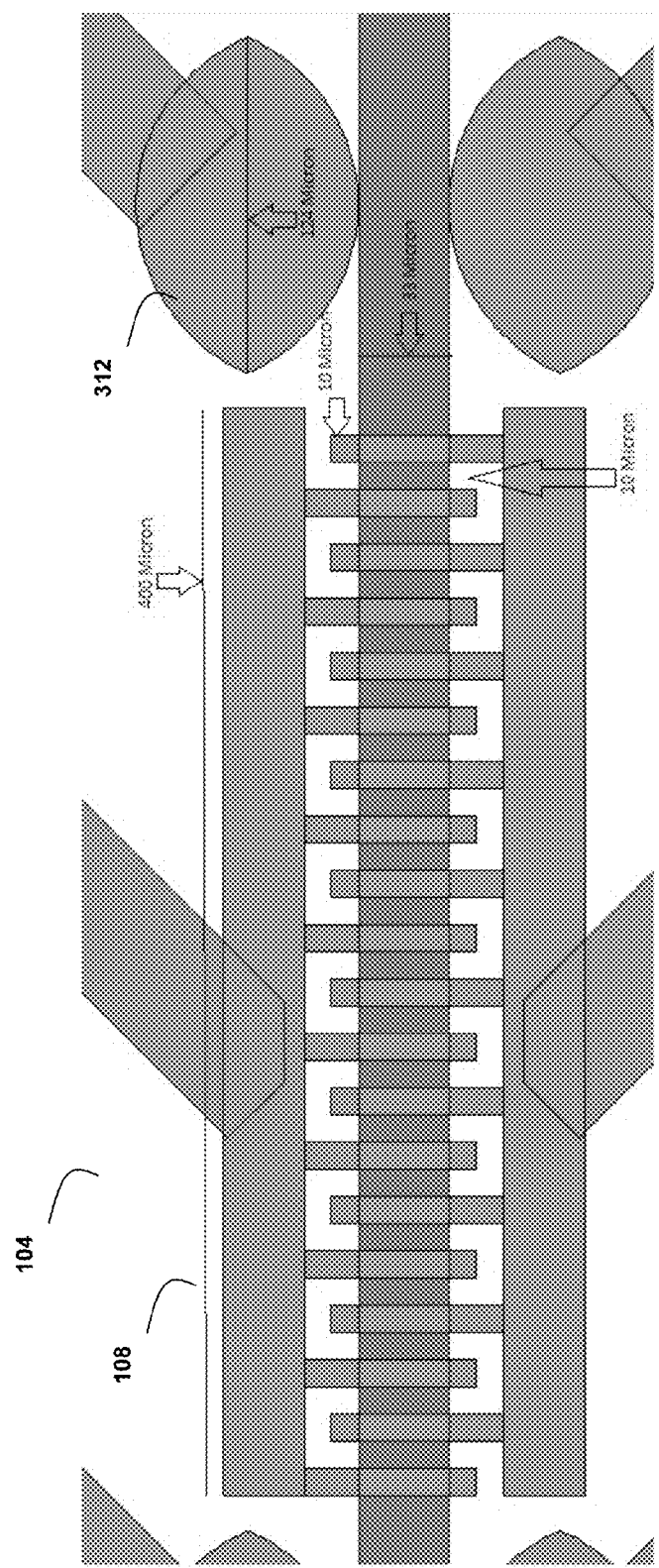
Figure 3G:
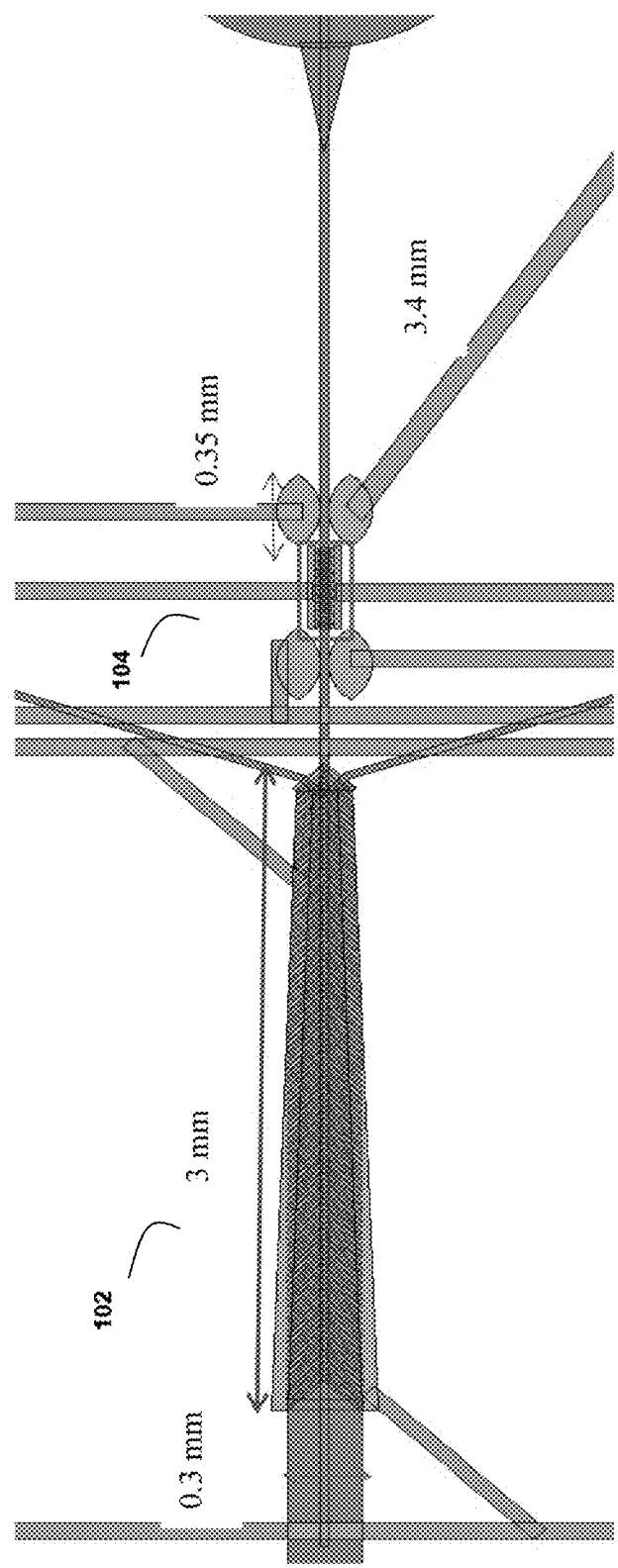

Returning to the example embodiment of FIG. 1, the focusing region 102 can have a width at its entrance of around 300 μm and a width at its exit of around 100 μm. The focusing region 102 may also have a length of around 3 mm and a height of around 20 μm or a value in a range between around 15-30 μm. In the example embodiment, the three branches that split off from the exit of the focusing region 102 can be dimensioned such that the center channel which serves as the detection region 104 can have a width of around 33 μm, while the two outer channels that serve as waste outlet branches can each have a width of around 34 μm. The length of the detection electrode array 108 within detection region 104 can be around 400 μm, and the length of each trapping electrode can be around 124 μm. Examples of this are shown by FIGS. 3E-3G However, it should be understood that other values for these dimensions could be employed by a practitioner.

Figure 3H:
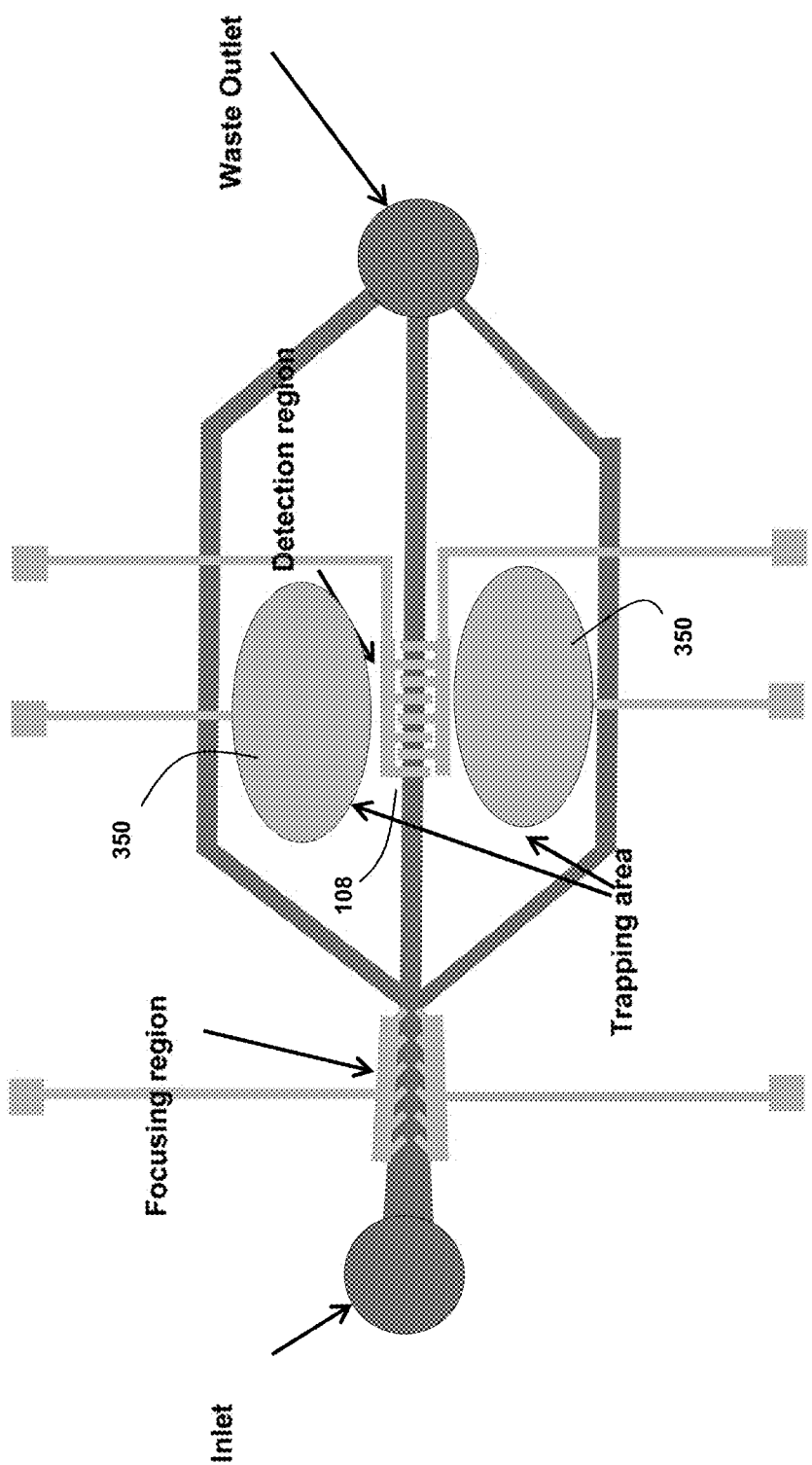
FIGS. 3H-3J depict another example embodiment for a trapping electrode array.
Figure 3I:
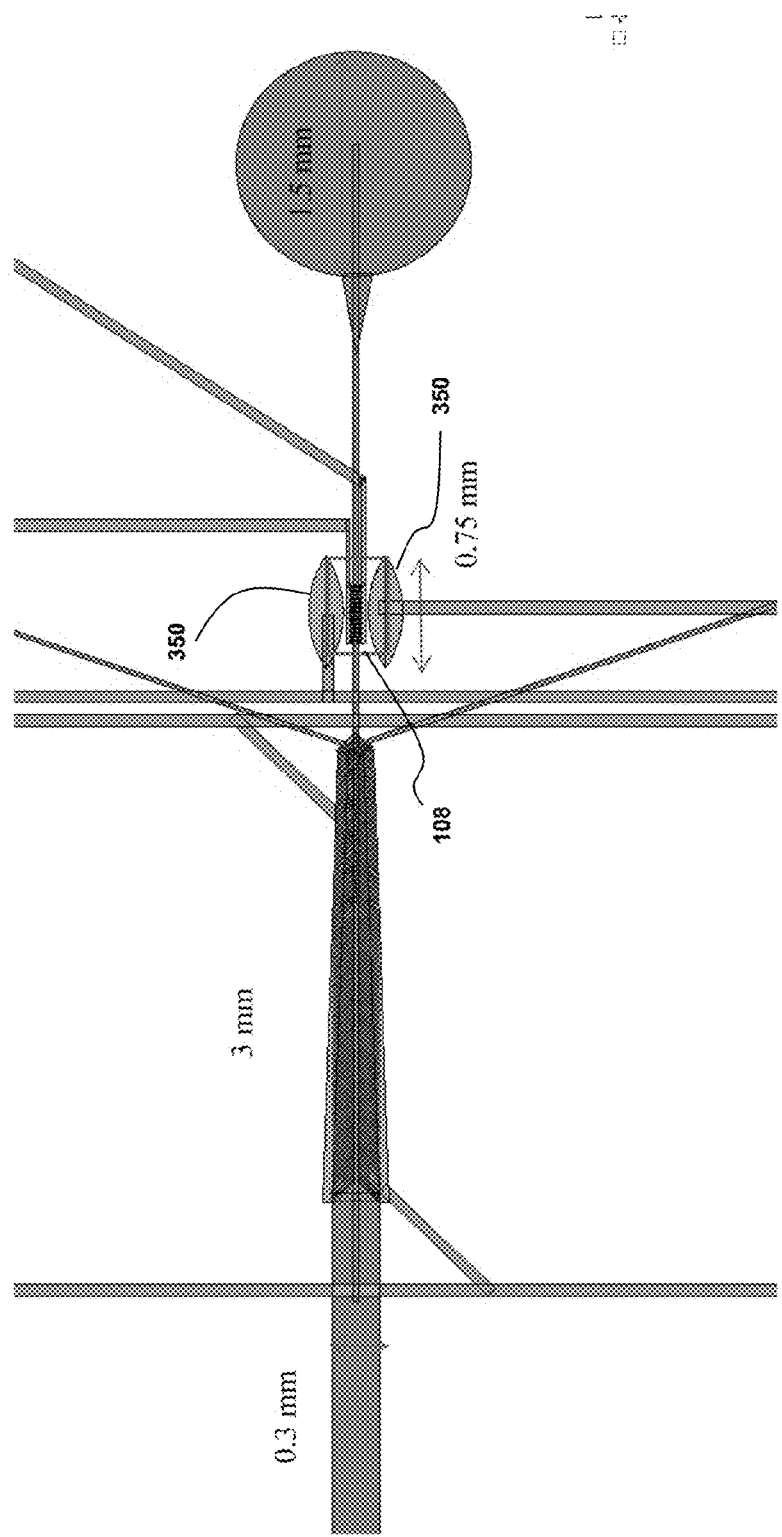
Figure 3J:
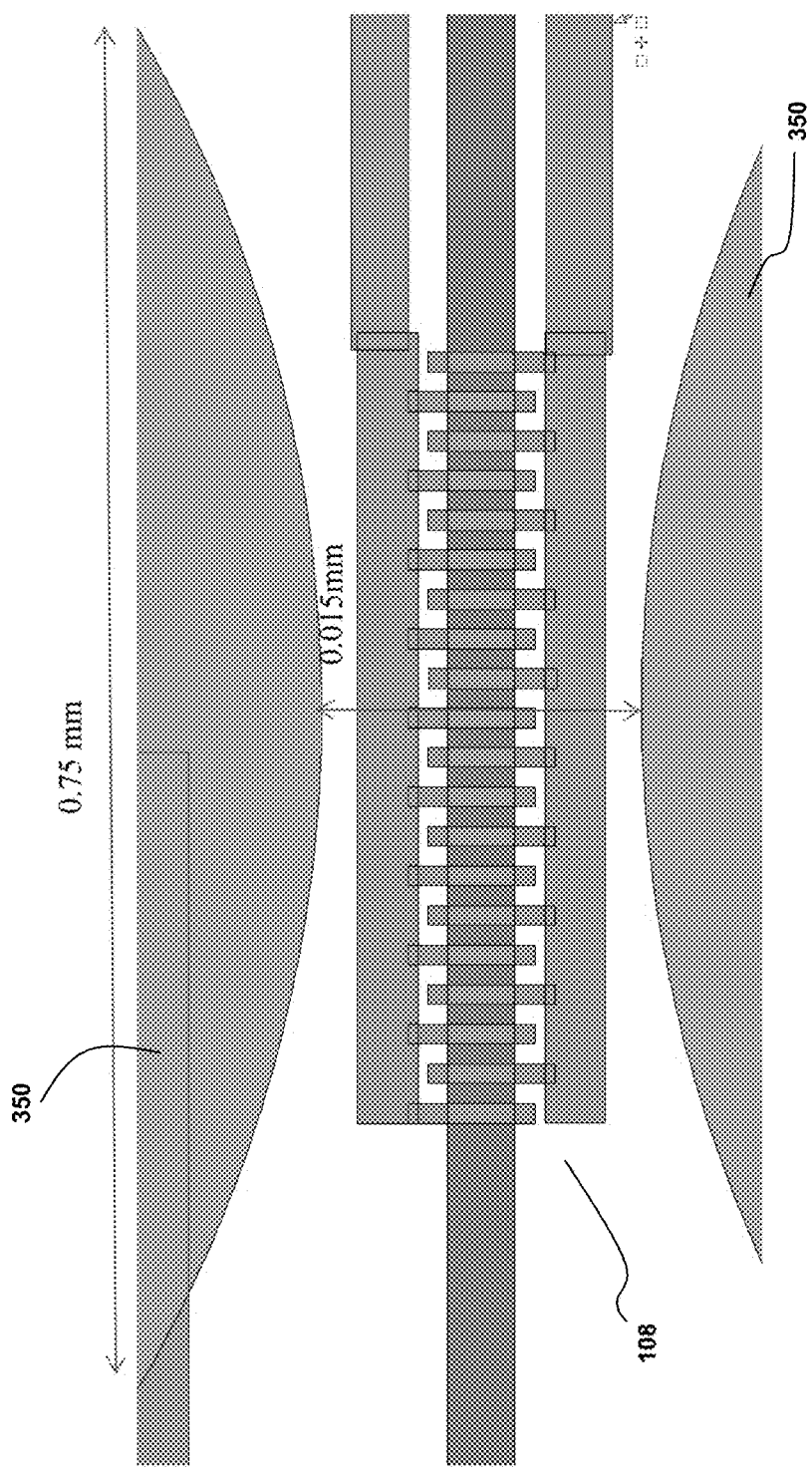

Furthermore, in another example embodiment, the trapping electrodes can be positioned to sandwich the detection electrode array 108 rather than bookend the detection electrode array. FIGS. 3H-3J show examples of such an arrangement. In these examples, the trapping region comprises an opposing pair of elliptically shaped vertical electrodes 350 that are positioned laterally outside the detection electrode array 108 (where the longitudinal direction corresponds to the flow direction through the microchannel) to effectively sandwich the detection electrode array 108, as shown by FIGS. 3H and 3I (where FIG. 3I shows example dimensions that can be used). Furthermore, FIG. 3J shows a zoomed-in view of the example embodiment of FIG. 3I. These electrodes 350 generate a high electric field that forces the substance of interest to move toward the region of high E-field using p-DEP in order to ensure an accumulation of the substance of interest on the detection electrode array 108.

Figure 4:
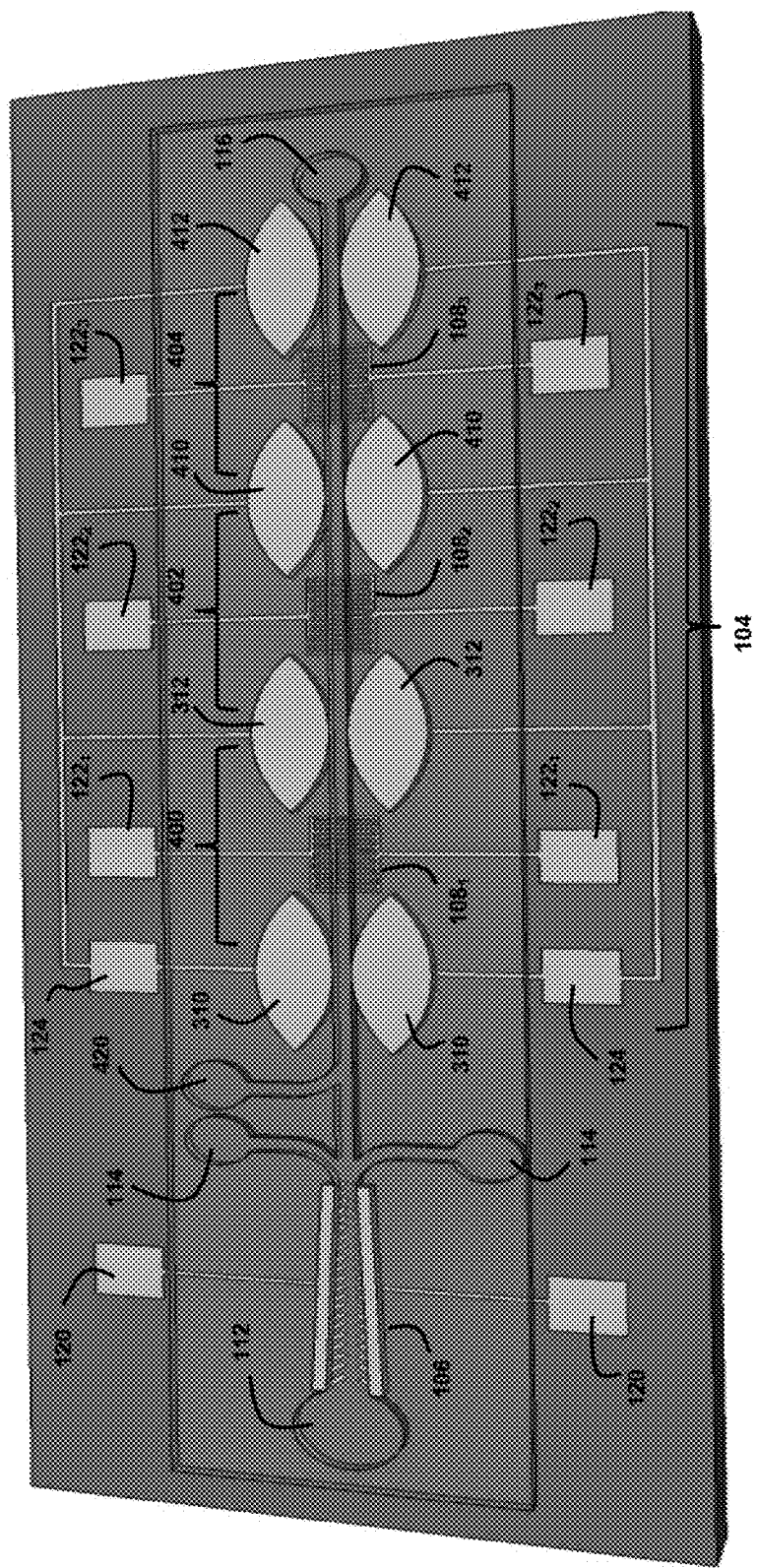
FIG. 4 depicts an example embodiment of a biosensor apparatus that includes multiple detection regions in series.

FIG. 4 depicts an example embodiment of a biosensor apparatus where the detection region 104 includes multiple detection regions 400, 402, and 404 in series. Each series detection region i includes its own detection electrode array $108_i$ (for example, detection region 400 includes detection electrode array $108_1$, detection region 402 includes detection electrode array $108_2$, and detection region 404 includes detection electrode array $108_3$). Each detection electrode array $108i$ has associated contacts/bonding pads $122i$ through which it connects with an impedance analyzer circuit. Each of the detection regions 400, 402, and 404 is separated from the adjacent detection region via trapping electrodes. Thus, detection region 400 is positioned between trapping electrodes 310 and 312, detection region 402 is positioned between trapping electrodes 312 and 410, and detection region 404 is positioned between trapping electrodes 410 and 412. Also shown by FIG. 4 is an antibody inlet 420 through which antibodies can be introduced into the detection regions 400, 402, and 404 in order to promote attachment of the bacteria of interest to the detection electrode arrays $108_1$, and $108_2$, and $108_3$.

The biosensor apparatus of FIG. 4 can be described with reference to an example use case where the apparatus is used to focus, trap, and detect low concentrations of E-coli within a fluid material with a volume on the order of pico liters. The sensor apparatus of FIG. 4 can be used to achieve a rapid detection with high selectivity for accurate identification of E. coli O157:H7 and sensitivity at a low concentration, 10 CFU/ml. The E. coli cells will be introduced via the fluidic inlet 112 into the focusing region that includes the focusing electrode array 106 (which uses a ramp down vertical electrode pair along with tilted thin film finger pairs (45°) with a ramp down channel) that generates p-DEP forces to focus and concentrate the cells into the center of the microchannel, and direct it toward the detection region microchannel which has a diameter as small as one-third of the focusing region channel with a nano liter volume. As the fluid exits the focusing region, the bulk fluid will keep flowing toward the outer channel into the waste outlets 114 while the concentrated mass of cells flows into the detection region. The solution with the concentration of *E. coli* subsequently enters into a narrower detection region channel which contains a series of 3 trapping and detection electrodes as discussed above. Once the detection region channel is full with the solution, the trapping electrodes 310, 312, 410, and 412 can be turned on for 15-20 minutes in order to trap the *E. coli* on top of the detection electrodes $108_1$, and $108_2$, and $108_3$. This region is connected to the outlet 116. As discussed above, the voltage at a specific frequency applied to the trapping electrodes will generate n-DEP forces that push the *E. coli* cells to the region of low E-field gradient and trap them on top of the detection electrodes $108_1$, and $108_2$, and $108_3$. This trapping mechanism will facilitate the binding process between *E. coli* (antigens) to *E. coli* (antibody, introduced via inlet 420) selectively on the IDE array(s). After turning off the trapping electrodes, the unbound antigens and other unwanted particles will be washed away using DI water. The impedance as a function of frequency will be recorded from each IDE array separately by an impedance analyzer. Through this impedance measurement, one can detect *E. coli* in the solution with a concentration of 10 CFU/ml with a high sensitivity and selectivity within 1 hour. The use of the series of 3 trapping and detection regions along the microchannel such that each electrode array records the impedance of *E-Coli* separately is expected to improve the sensor's sensitivity. The use of these arrays help ensure the capturing of *E-Coli* cells by one or more detection electrode arrays. When *E. coli* binds to antibodies, only a region of 2-4 µm above the sensor surface will be modified. The biosensors will then be washed in DI water to remove the unbound or weakly bound *E. coli* cells to the immobilized antibodies and cleans the debris (such as salts) from the sensor interior surface.

The biosensor apparatus of FIG. 4 can be fabricated using techniques shown in connection with FIGS. 8A-G. In this example, the biosensor apparatus can be fabricated on a glass substrate 800 using a series of photolithography, electroplating, and surface micromachining in the following steps:
1) Thin films of Chromium (Cr) (804) and Goal (Au) (806) are sputtered on a glass substrate (800) coated with a thin layer of SU-8 2005 (802) (see FIG. 8A).
2) The Au (806) layer is patterned on the SU-8 2005 (802) layer to create the electrodes interdigitated electrode arrays, traces, bonding pads, and seed layer for electroplating the focusing electrode (see FIG. 8B).
3) A photoresist mold (e.g., AZ 4620 (810) is patterned for Au (see FIG. 8C).
4) Au (806) is then electroplated to create the vertical side wall electrodes (see FIG. 8D).
5) The photoresist mold (810) is removed and the Cr (804) layer is etched 9 (see FIG. 8E).
6) SU-8 2025 (808) is spincoated and patterned to create the microfluidic channel. Also, Au (806) is deposited to create the trapping electrodes (see FIG. 8F)
7) A PDMS (812) cover with inlet/outlet holes for the fluidic connectors 814 is cured and bonded to the microchannel layer using an $O_2$ plasma technique (see FIG. 8G).

Figure 5:
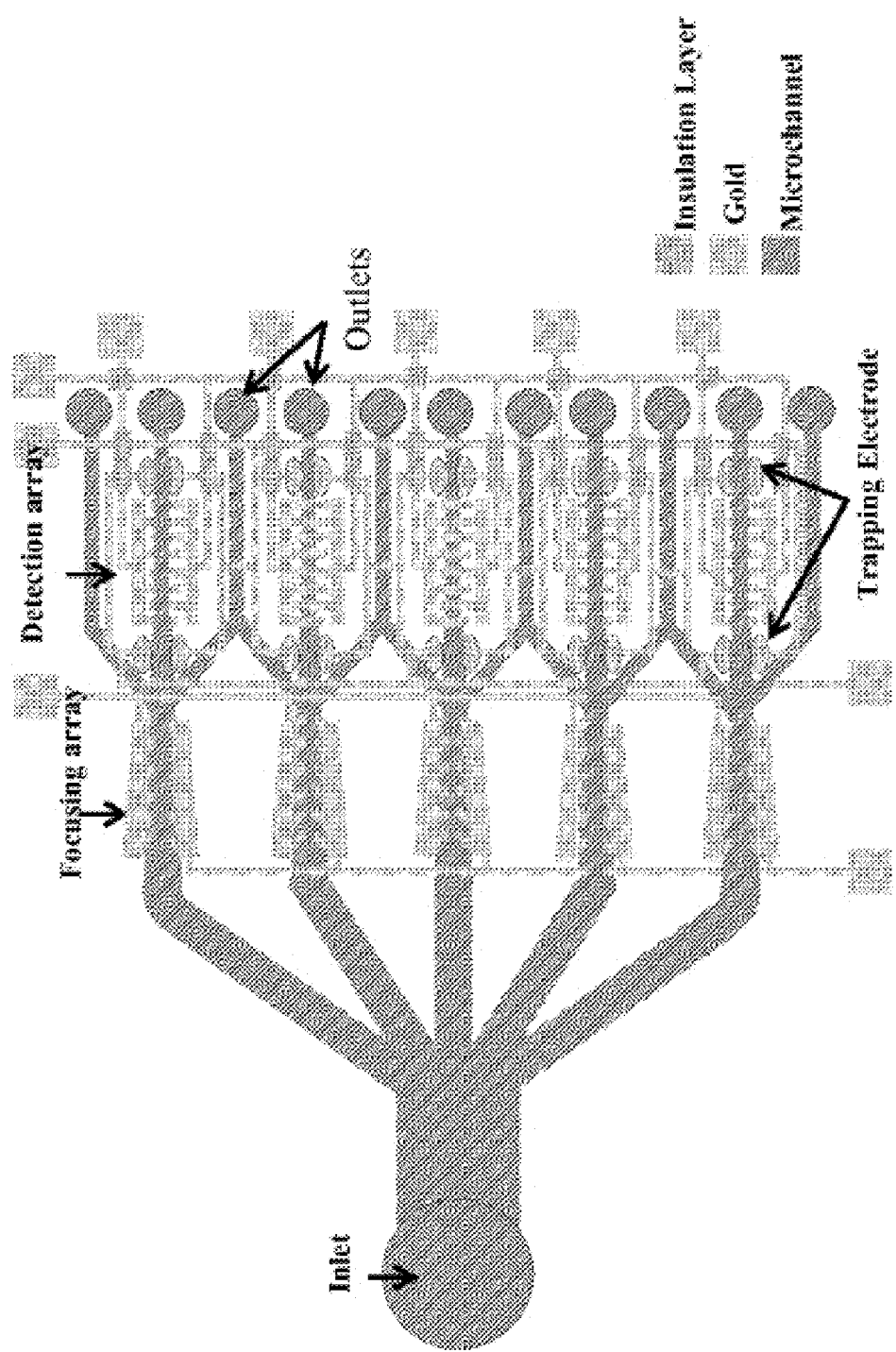
FIG. 5 depicts an example embodiment of a biosensor apparatus that includes multiple focusing and detecting regions in parallel.

FIG. 5 depicts an example embodiment of a biosensor apparatus that includes multiple focusing regions 102 and multiple detection regions 104 in parallel. A flow of the fluid material is split into multiple paths upstream from the focusing regions, and each path includes a focusing region 102 followed by a downstream detection region, as shown by FIG. 5.

Figure 6:
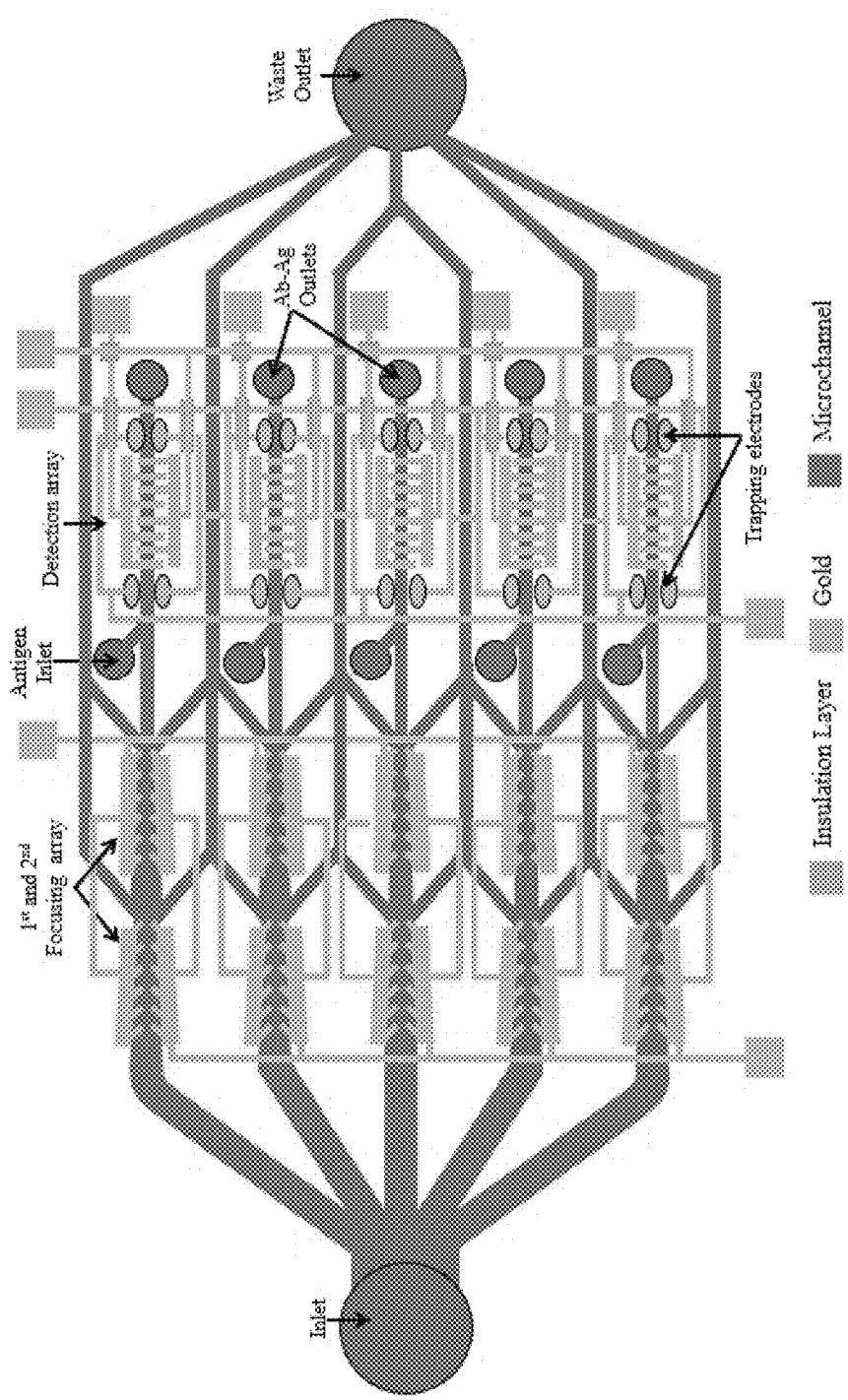
FIG. 6 depicts another example embodiment of a biosensor apparatus that includes multiple focusing and detecting regions in parallel.

FIG. 6 depicts another example embodiment of a biosensor apparatus that includes multiple focusing regions 102 and multiple detection regions 104 in parallel. In the example of FIG. 6, the focusing region 102 includes a plurality of focusing electrode arrays 106 in series (e.g., 2 focusing electrode arrays 106 in series). In this example pathogen detection system, the sensitivity is increased by increasing the ratio of pathogen bacteria cells to test media volume. The ratio is increased drastically by getting rid of 80% volume of the test media. This is achieved by sequential focusing of bacteria cells towards the center of the microchannel with the help of two stages of the focusing electrode arrays 106 within each path. Each focusing electrode array 106 can be configured as discussed above in connection with FIGS. 2A and 2B. Using the DEP principle and the unique configuration of thick-thin electrodes (e.g., where the thickness/height of the microchannel is 15 µm), each focusing electrode array 106 generates a non-uniform distribution of electric field across the channel width. This along with fluidic drag force, helps focus the pathogen bacteria cell towards the center of the microchannel.

The initial width of the channel at the inlet/port can be 500 µm in the example of FIG. 6. The inlet channel is then divided into five equal paths, each with 100 µm width. After the $1^{st}$ focusing electrode array 106, each path is further split into three channels with the outer two channels and the center channel being 30 µm and 40 µm in width, respectively. The outer two channels are connected to the main waste outlet-port to get rid of extra test media. The center channel carries the focused bacteria cells through the $2^{nd}$ focusing electrode array 106. After the $2^{nd}$ focusing electrode array, the 40 µm center channel is once again divided into three channels to get rid of more test media, while concentrating the bacteria towards the center of the microchannel. The outer two channels and the center channel being 12 µm and 16 µm in width, respectively. The 12 µm wide outer channels are also connected to the main waste outlet-port. The 16 µm center channel carries the concentrated bacteria cells towards the detection electrode array 108 for that path.

The detection electrode arrays 108 are functionalized with pathogen bacteria specific antibodies and configured as discussed above in connection with FIG. 3A. As the bacteria come in contact with the antibody, they bind to the surface of the interdigitated electrode decreasing the exposed surface of the electrodes. Decreased surface area of the detection electrodes reduces the overall capacitance of the system and results in an increase of impedance. The concentration of pathogen bacteria cell present in the test media can be correlated to the change in impedance.

Figure 7A:
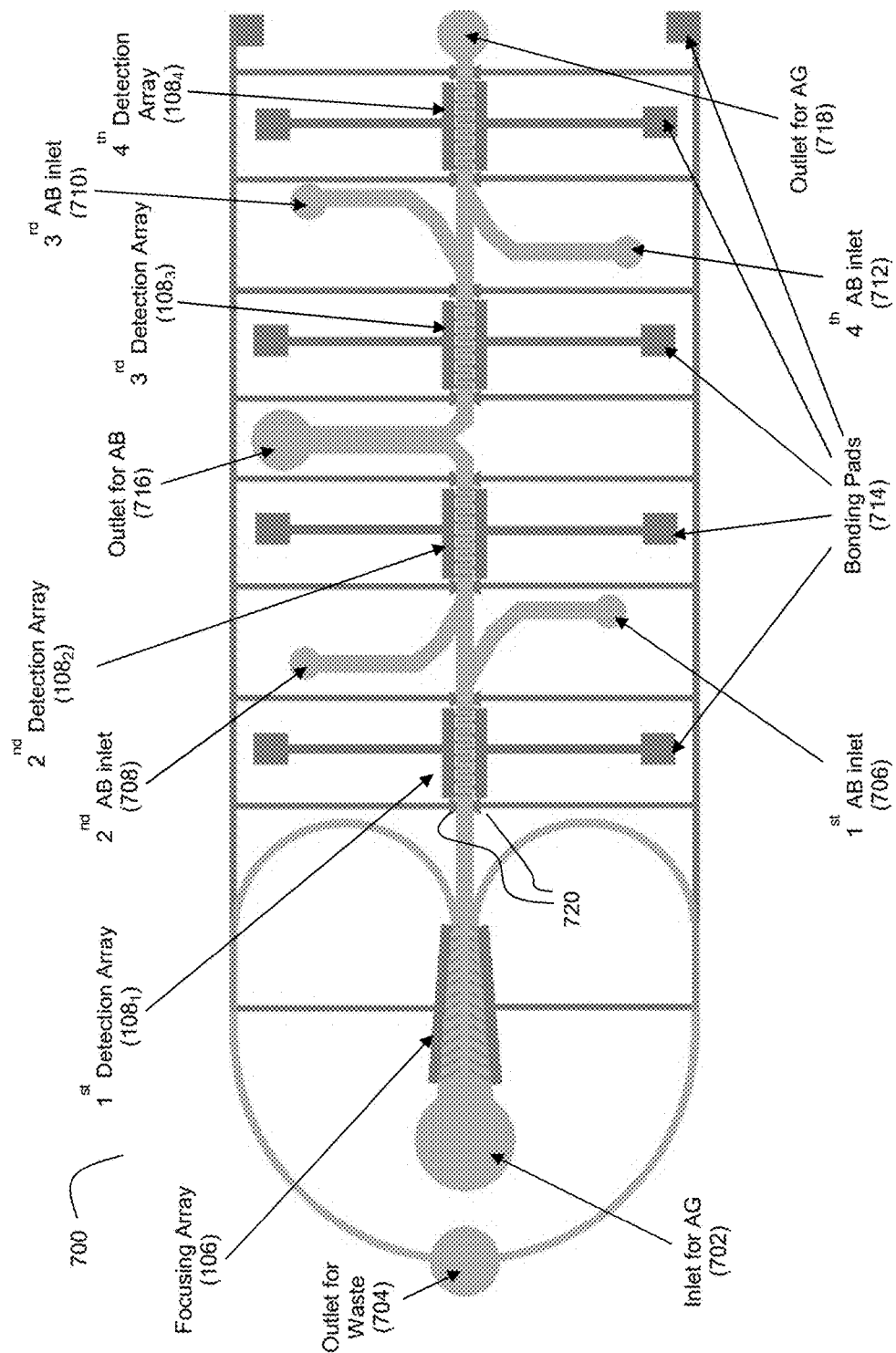
FIGS. 7A and 7B depict another example embodiment of a biosensor apparatus that includes multiple detection regions in series.
Figure 7B:
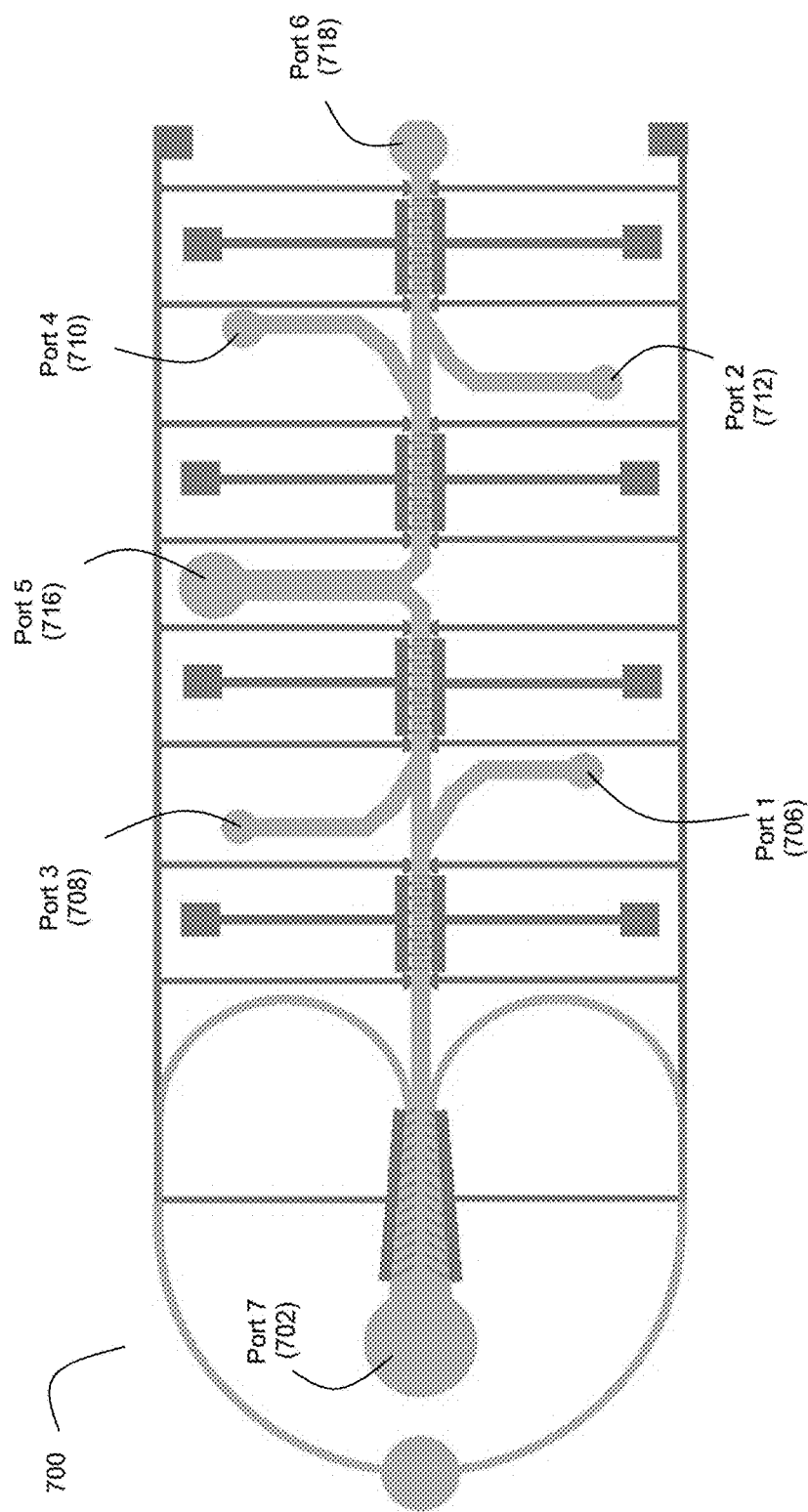

FIGS. 7A and 7B depict another example embodiment of a biosensor apparatus 700 that includes multiple detection regions in series and is capable of detecting different kinds of bacteria. In this example, each of the four different detection electrode arrays $108_1$, $108_2$, $108_3$, and $108_4$ can be coated with four different kinds of antibodies introduced via antibody inlets 706, 708, 710, and 712 respectively. Then the sample comes into the detection channel through the focusing electrode array 106 after unwanted waste has been filtered out (into waste outlet 704) and a concentration of the bacteria is passed into the detection region. By appropriately applying pressure, one can prevent cross-contamination of the four different antibodies. For example, two different antibodies can be delivered via ports 706 and 712. Negative pressure is then applied from ports 702 and 718 which causes (1) the antibody introduced via port 706 to come into contact with detection electrode array $108_1$ while the negative pressure prevents that antibody from coming into contact with detection electrode array $108_2$, and (2) the antibody introduced via port 712 to come into contact with detection electrode array $108_4$ while the negative pressure prevents that antibody from coming into contact with detection electrode array $108_3$. Then, two more different antibodies can be delivered via ports 708 and 710 while negative pressure is applied from port 716. The negative pressure applied from port 716 causes (1) the antibody introduced via port 708 to come into contact with detection electrode array $108_2$ while the negative pressure prevents that antibody from coming into contact with detection electrode arrays $108_1$ and $108_3$, and (2) the antibody introduced via port 710 to come into contact with detection electrode array $108_3$ while the negative pressure prevents that antibody from coming into contact with detection electrode array $108_2$ and $108_4$.

After the detection electrode arrays 108 have been properly coated with their respective antibodies, the antigen sample can be introduced via inlet port 702. Negative pressure is applied at outlet port 718 while keeping the other outlets/inlets closed to cause the antigen sample to pass through the focusing electrode array 106 and the four detection electrode arrays 108. Thus, it can be seen that a design such as that shown by FIGS. 7A and 7B can be used to test the same sample for different bacteria of interest via the same sensor apparatus 700.

Figure 7C:
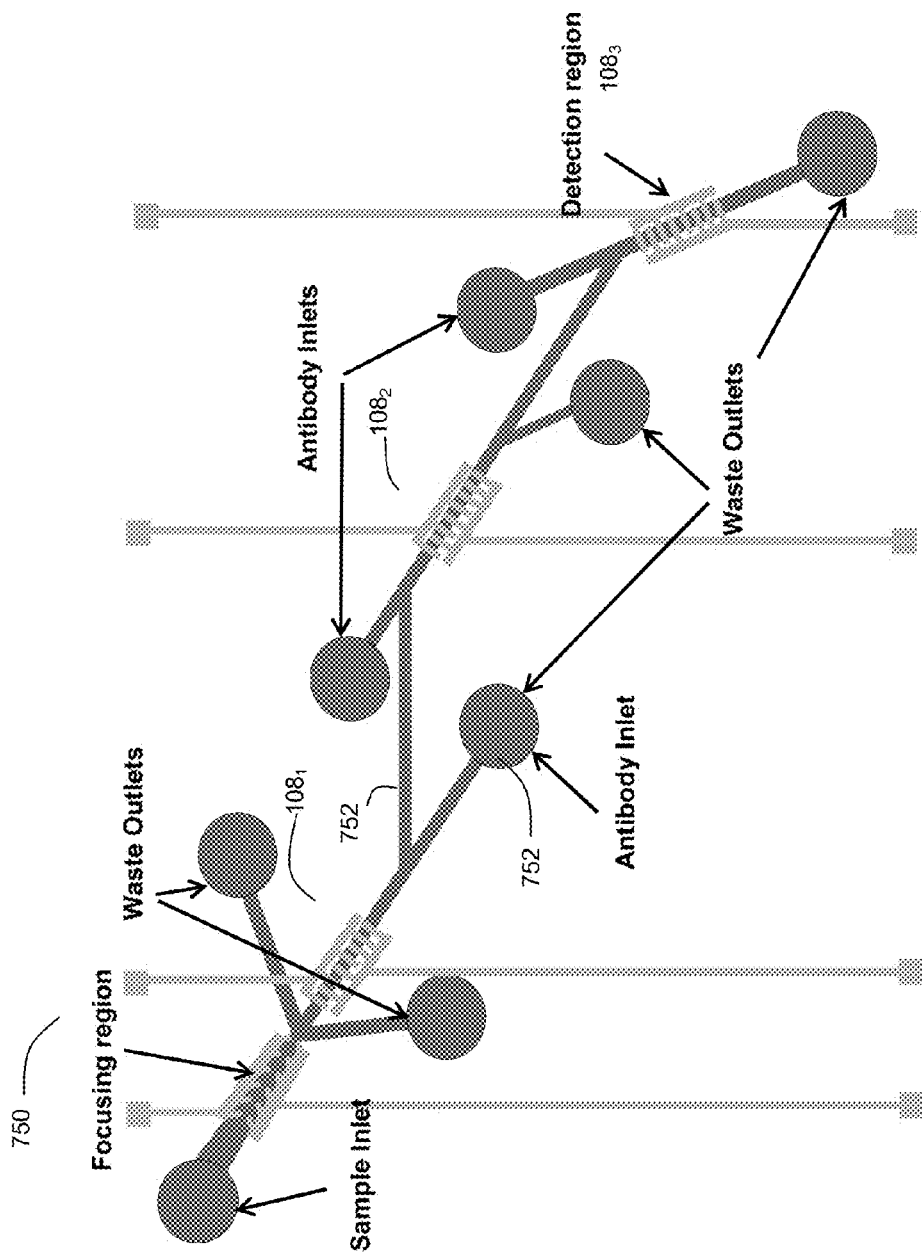
FIG. 7C depicts another example embodiment of a biosensor apparatus that includes multiple detection regions in series.

FIG. 7C depicts another example embodiment of a biosensor apparatus 750 that includes multiple detection regions in series and is capable of detecting different kinds of bacteria. Unlike the example of FIGS. 7A and 7B, the different detection regions 108 are not aligned on the same longitudinal axis of a straight line flow path. In the example of FIG. 7C, detection region $108_1$ is aligned with the focusing region, but an angled branch 752 splits off from the exit of detection region $108_1$, which then again angles into detection region $108_2$. It can also be seen that port 752 can serve as both an antibody inlet and a waste outlet with respect to detection electrode region $108_1$. An antibody inlet feeds into and is aligned with detection region $108_2$ while a waste outlet meets the exit of detection region $108_2$ at an angle. Also meeting the exit of detection region $108_2$ at an angle is the entrance to detection region $108_3$. An antibody inlet feeds into and is aligned with detection region $108_3$ while a waste outlet is aligned with the exit from detection region $108_3$.

The sensor apparatus 750 of FIG. 7C works first by injecting a specific antibody from a corresponding inlet to be immobilized on the detection regions, where the measurement is conducted. This unique series design allows the use of multiple antibody types on the same channel by incorporating three different inlets and three different outlets with the main channel with specific arrangement to prevent the mixture of the antibody types. As with the example of FIGS. 7A and 7B, selective pressurization can be used to prevent cross-contamination of antibodies into the different detection electrode regions $108i$. Once the antibody types settle down, the antigen sample will be injected and the focused to the detection channel and get rid of the bulk flow. To collect the antigens after testing is complete, water can be injected from the waste ports for detection electrodes $108_{1-3}$. The antigens can be collected via antibody inlet for detection electrodes $108_2$ and $108_3$ and sample inlet for detection electrode $108_1$. After the antigen bonded with the antibody, the impedance of the electrodes will be measured and the difference in impedance presents the existence of the antigen sample.

Figure 7D:
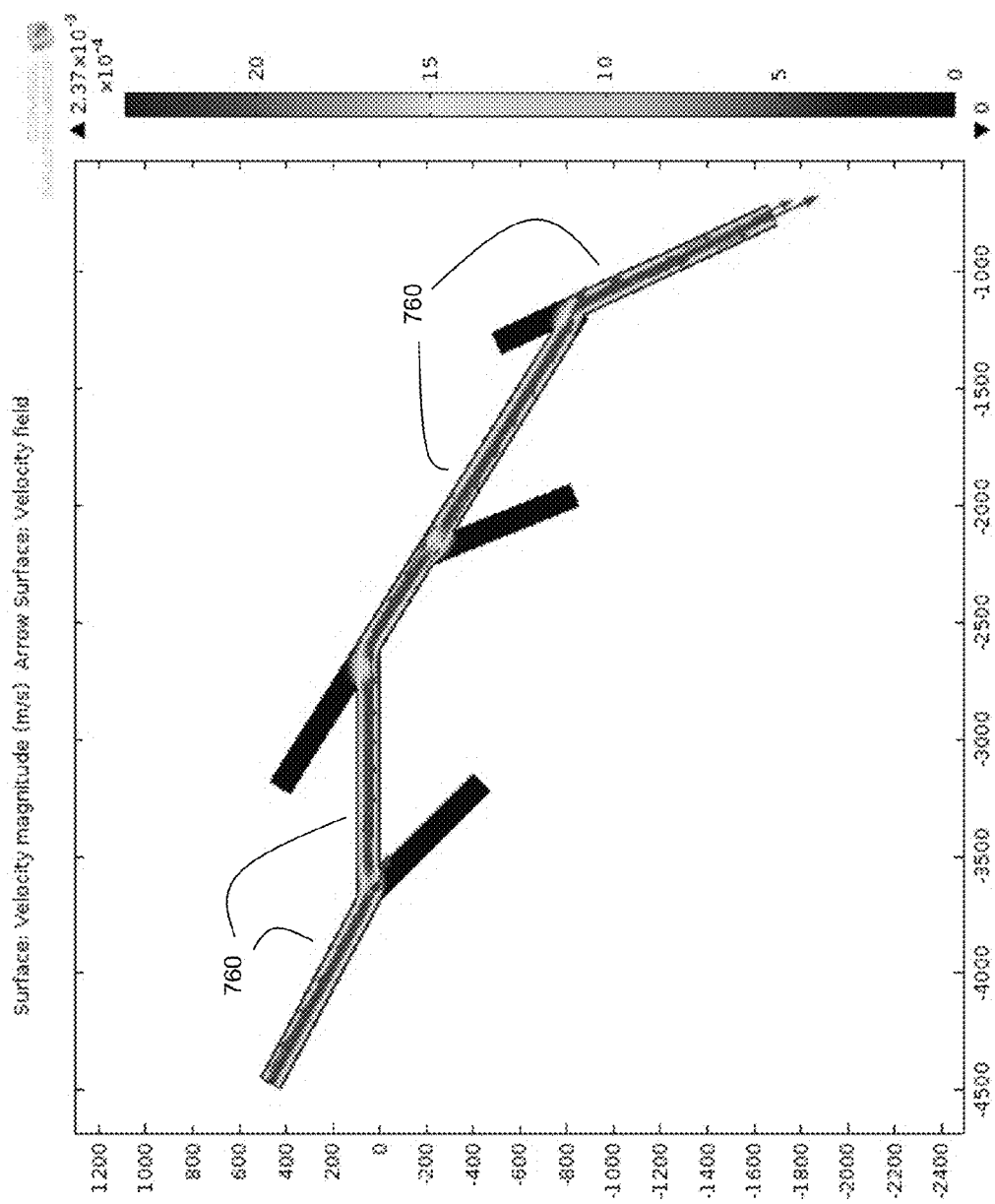
FIGS. 7D-7F shows simulation views of an example flow through the sensor apparatus of FIG. 7C.
Figure 7E:
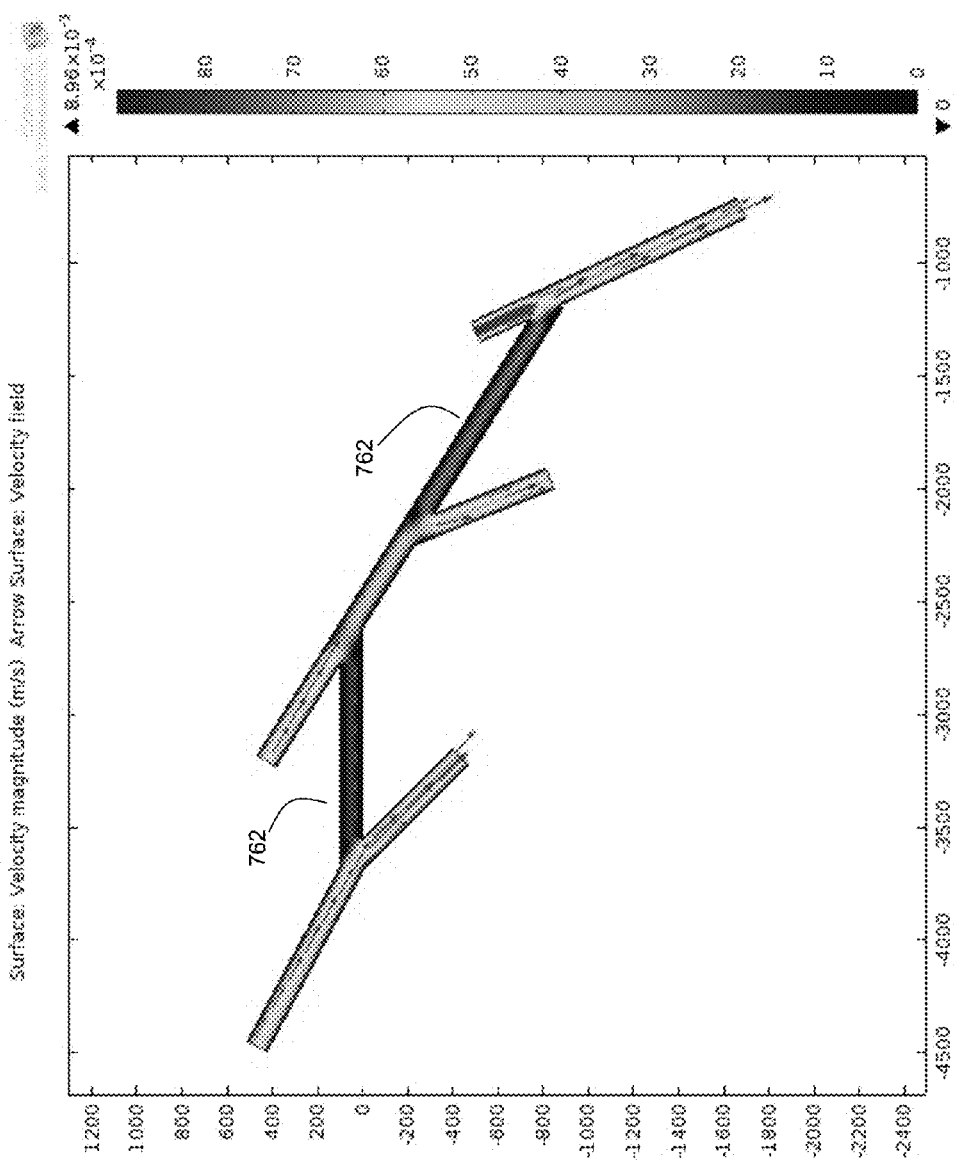
Figure 7F:
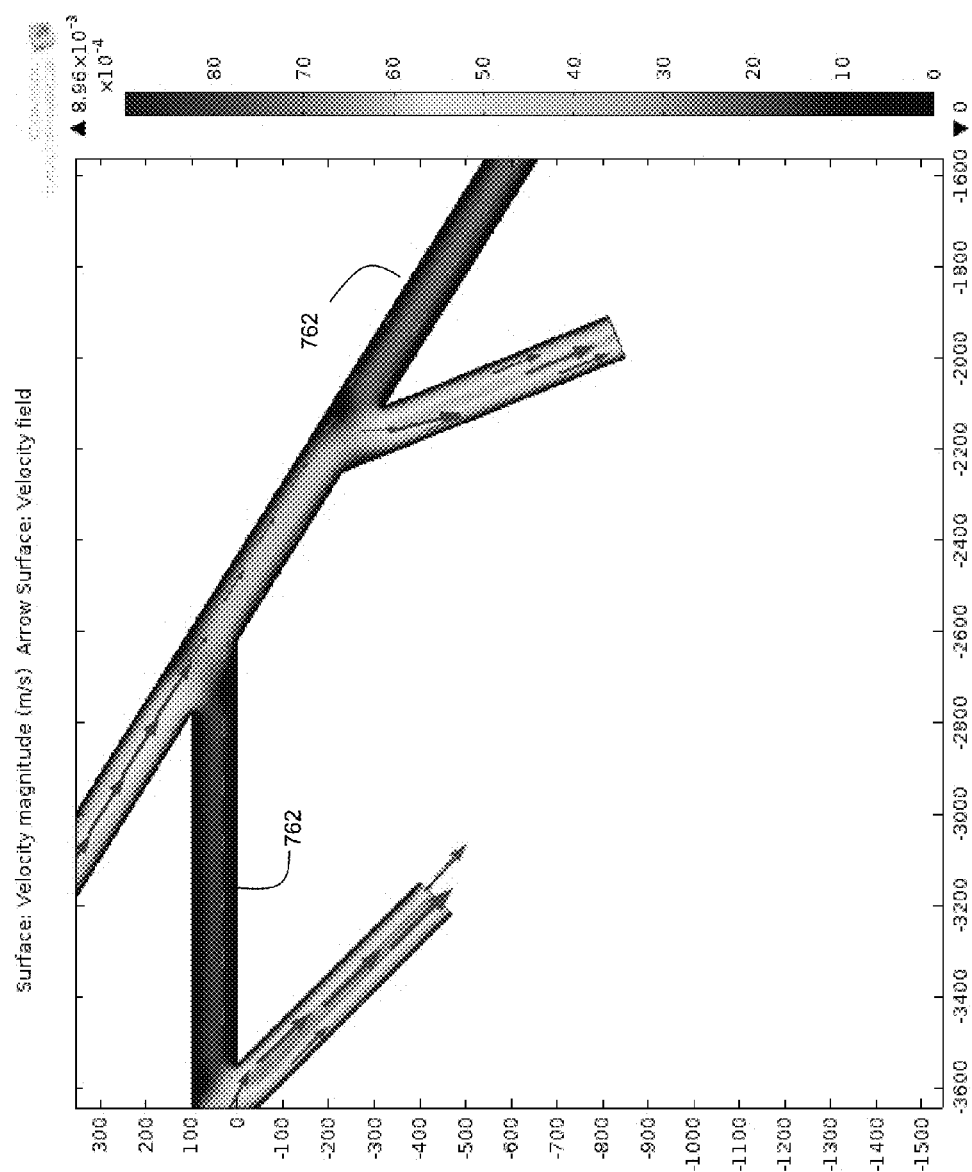
Figure 8A:
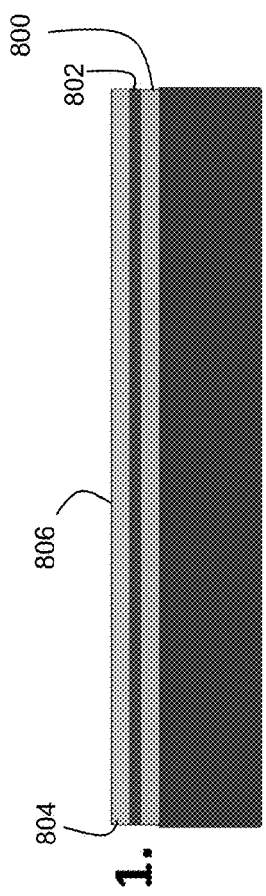
Figure 8A:
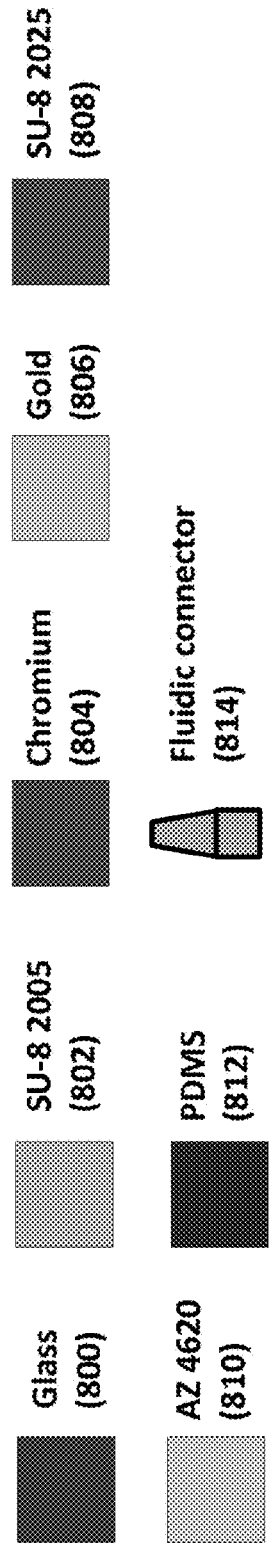
Figure 8B:
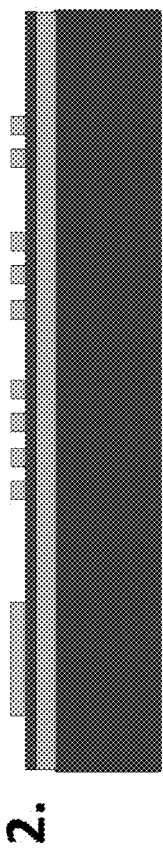
Figure 8C:
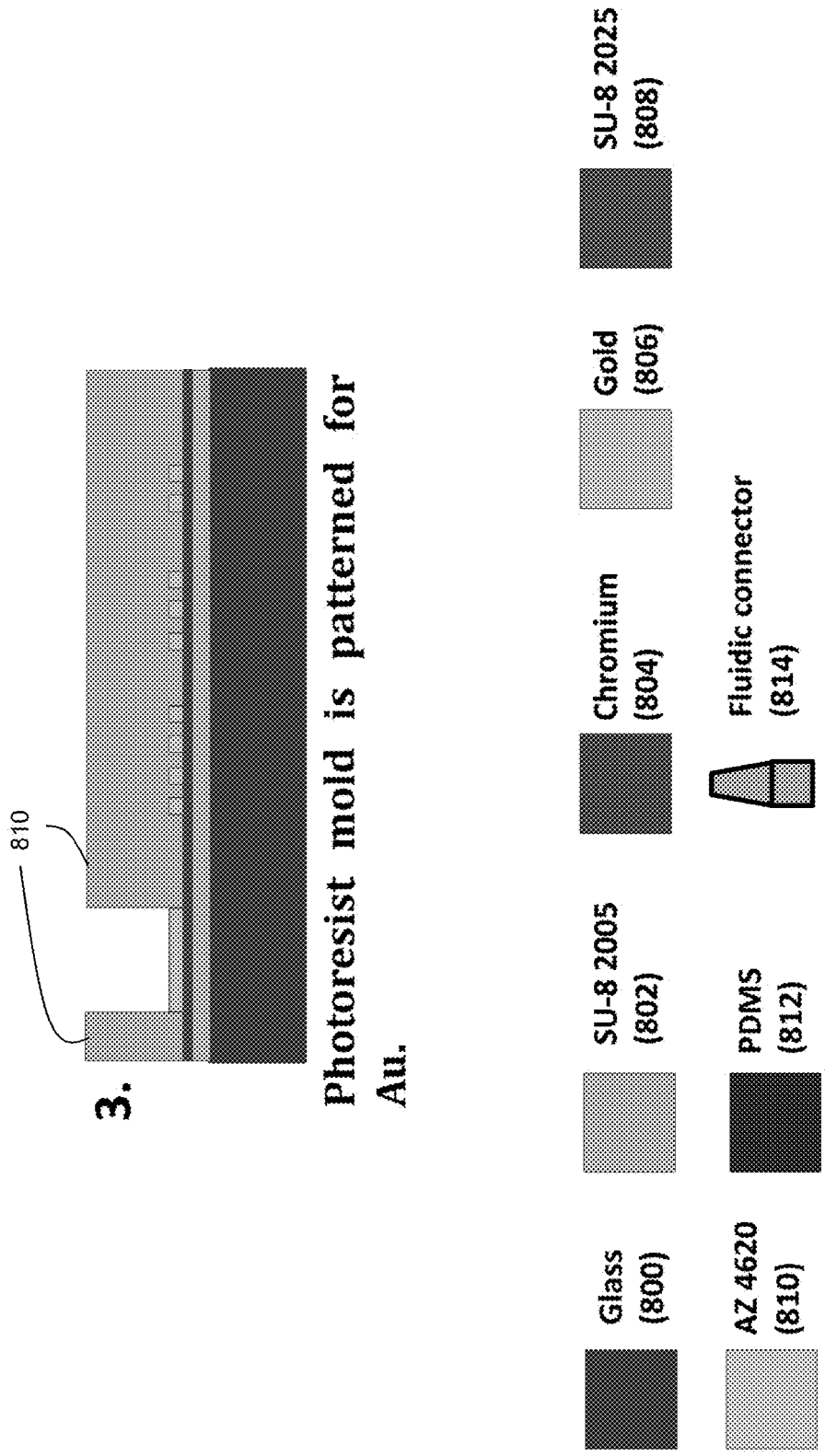
Figure 8D:
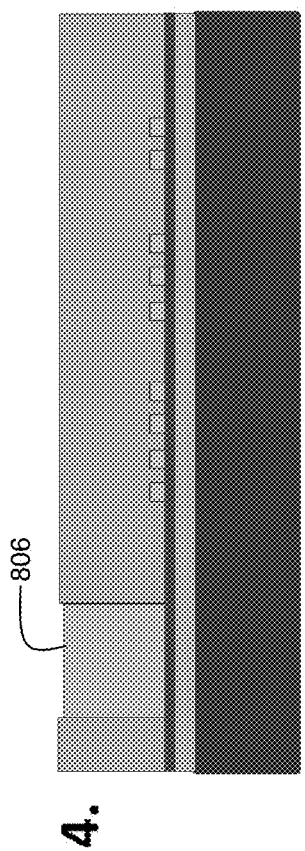
Figure 8D:
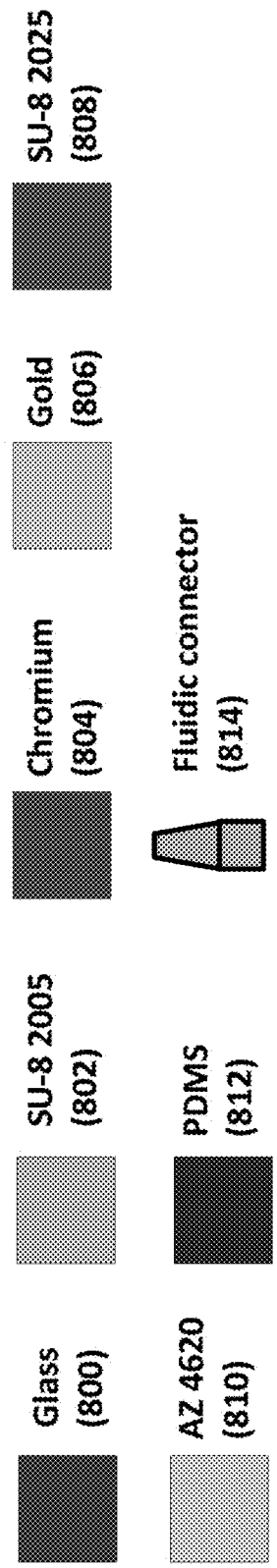
Figure 8F:
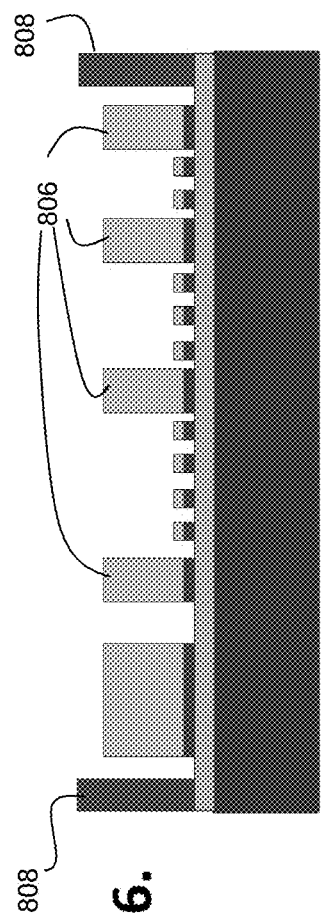
Figure 8F:
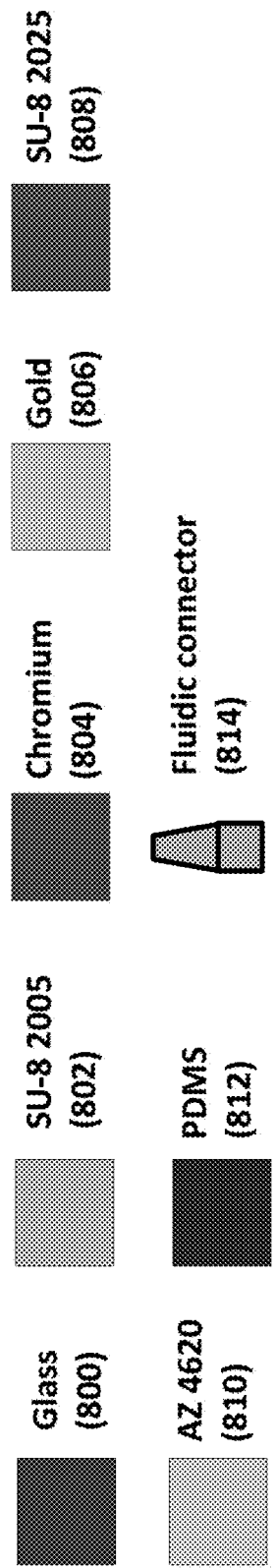
Figure 8G:
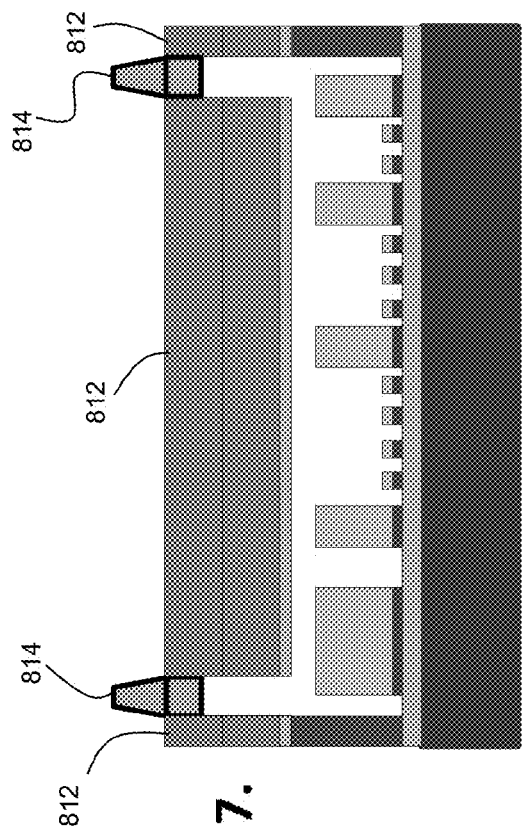

FIGS. 7D-F shows simulation views of an example flow through the sensor apparatus 750. FIG. 7D shows the flow of the sample via flow path 760. For this example flow, all inlets were closed with the exception of the last outlet. FIG. 7E shows the flow path for the introduction of an antibody, and there areas of no flow are shown by 762. As can be seen, these areas 762 present cross-contamination of the different detection electrode regions. FIG. 7F shows a zoomed view of FIG. 7E.

Figure 9A:
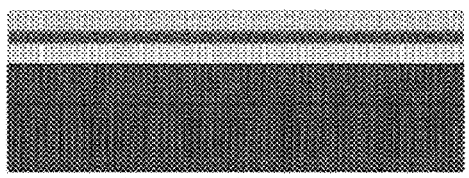
FIGS. 9A-9H depict an example fabrication process for a biosensor apparatus in accordance with another example embodiment.
Figure 9A:
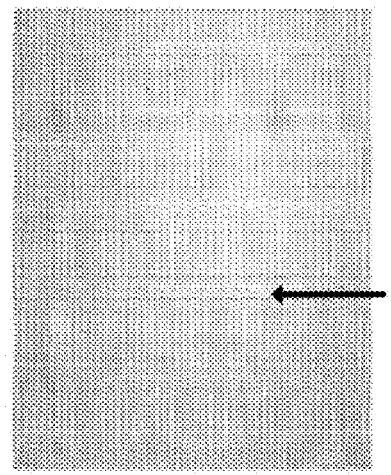
Figure 9A:
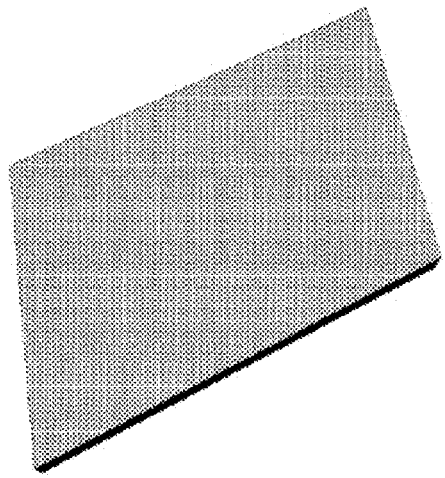
Figure 9B:
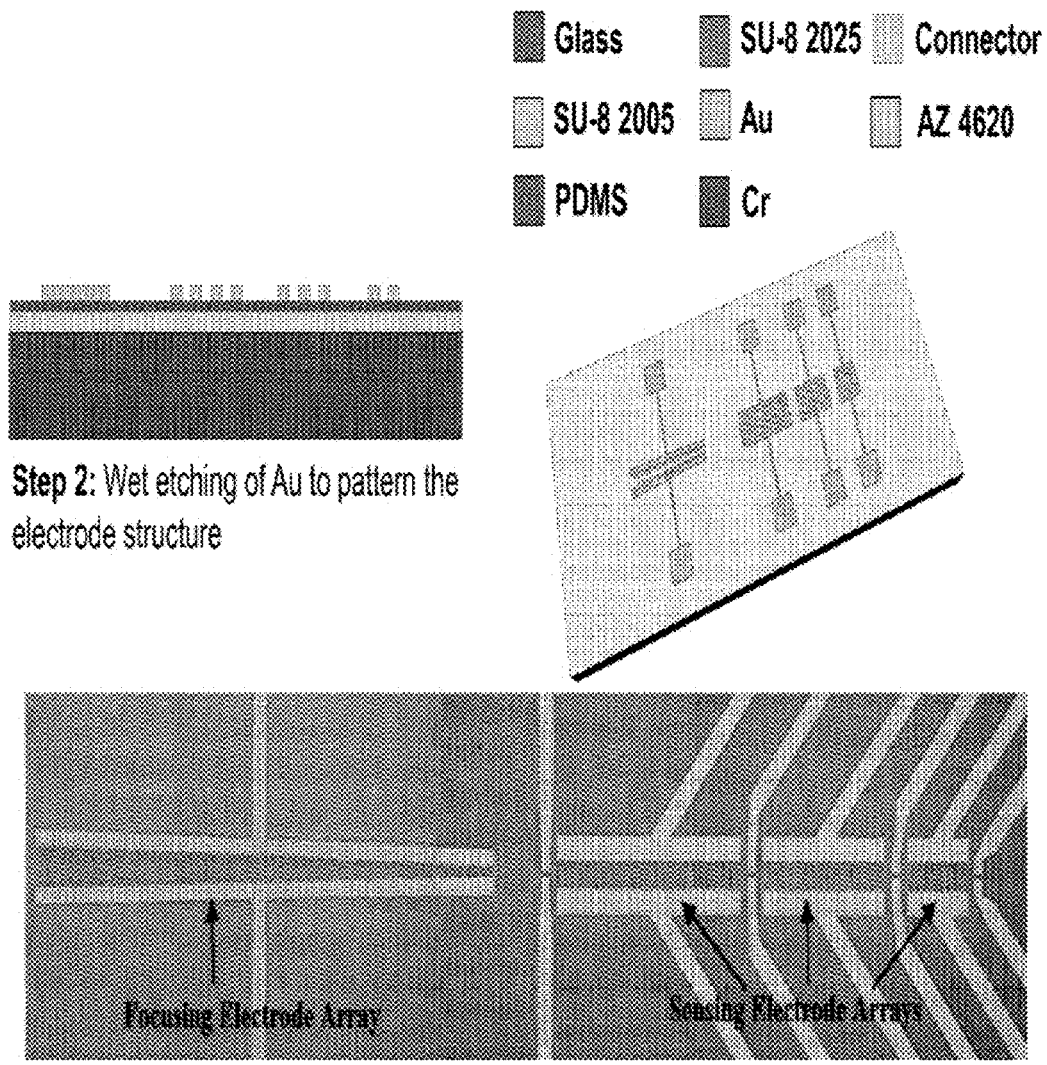
Figure 9C:
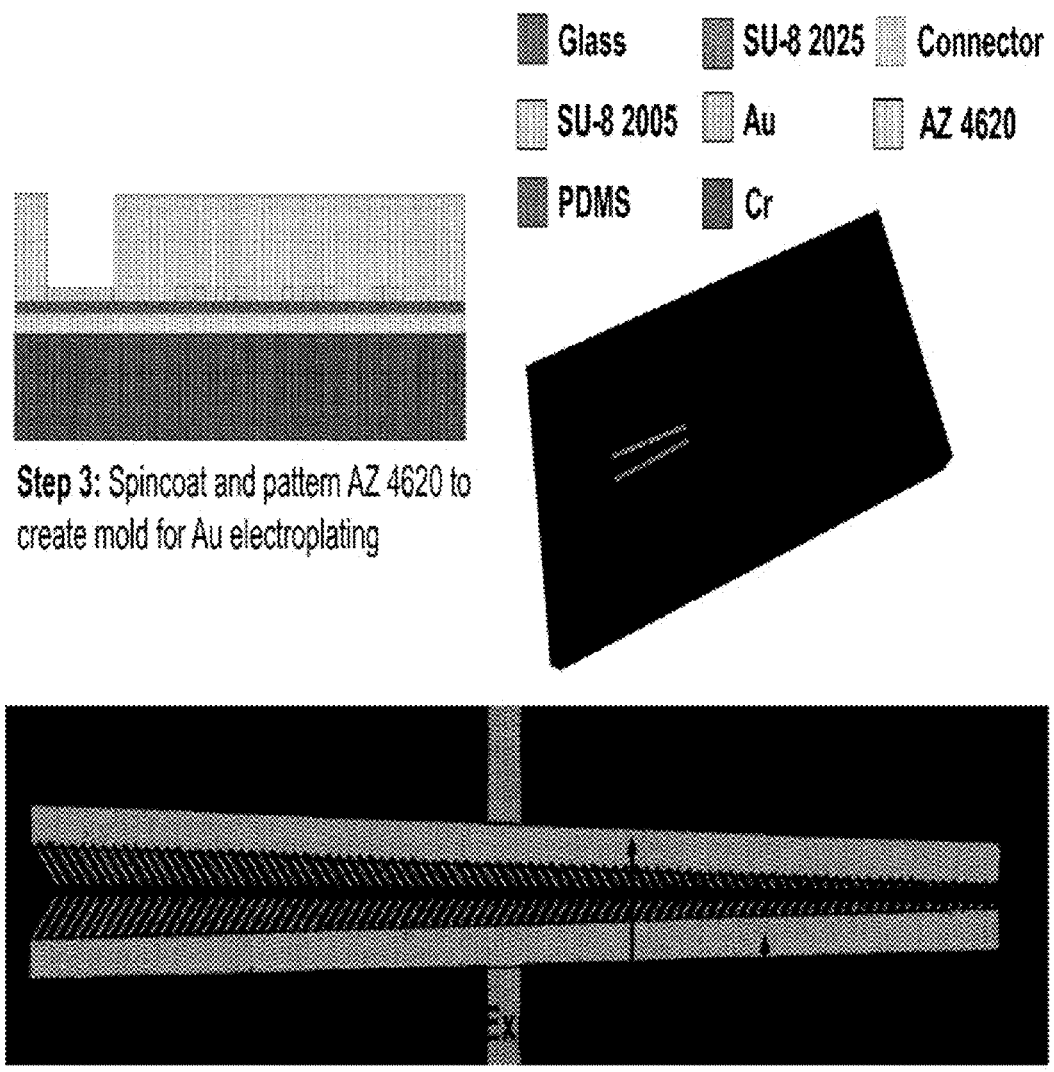
Figure 9D:
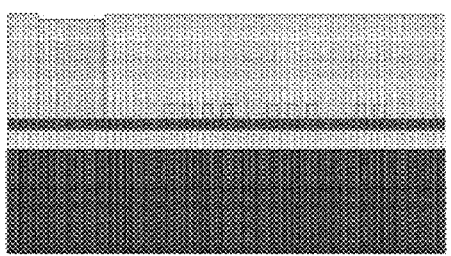
Figure 9D:
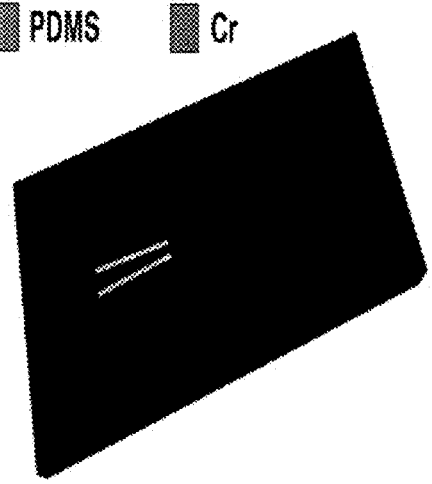
Figure 9D:
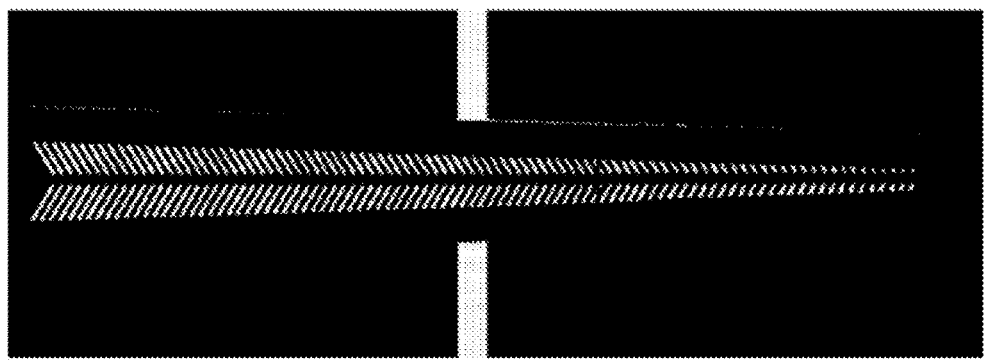
Figure 9E:
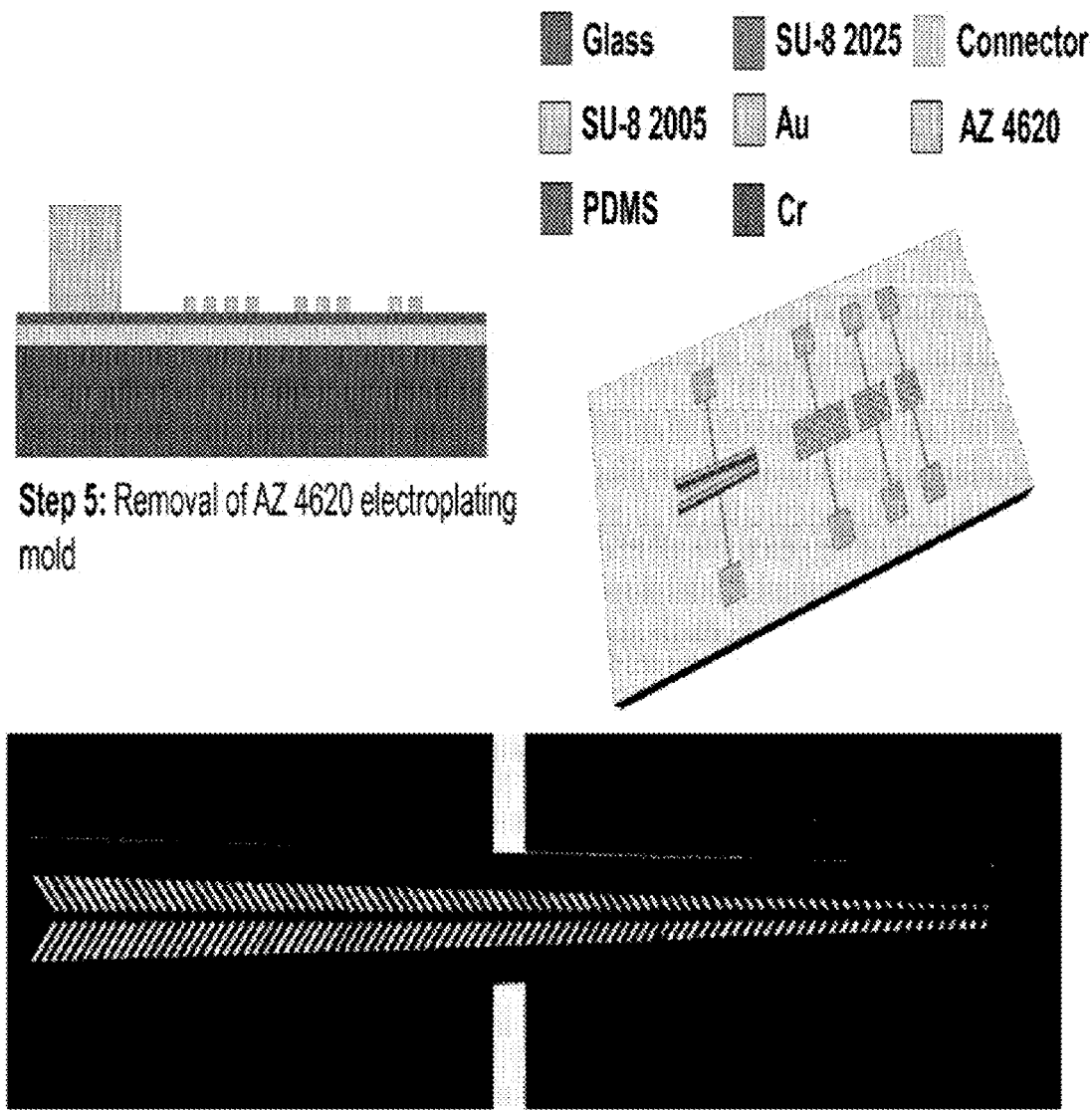
Figure 9F:
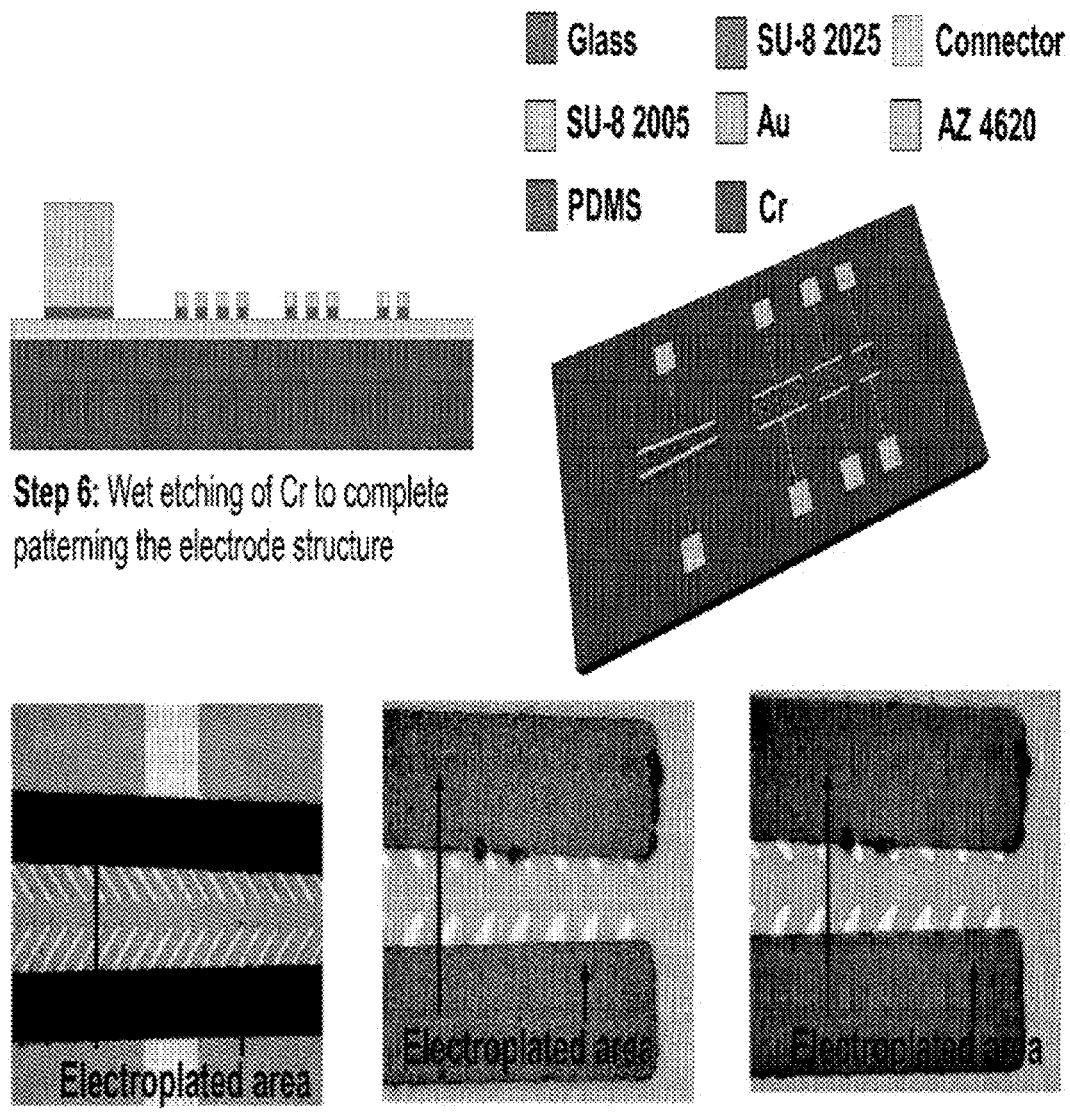
Figure 9G:
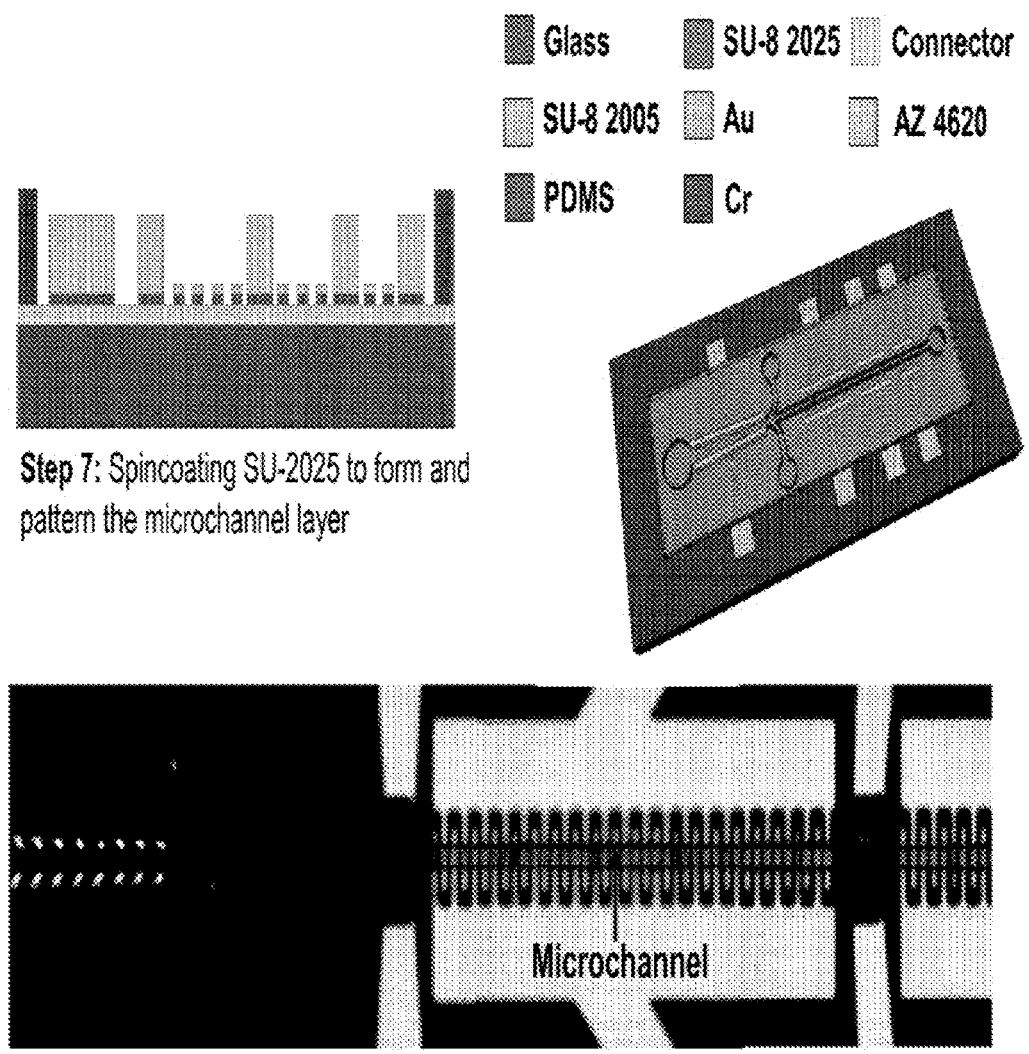
Figure 9H:
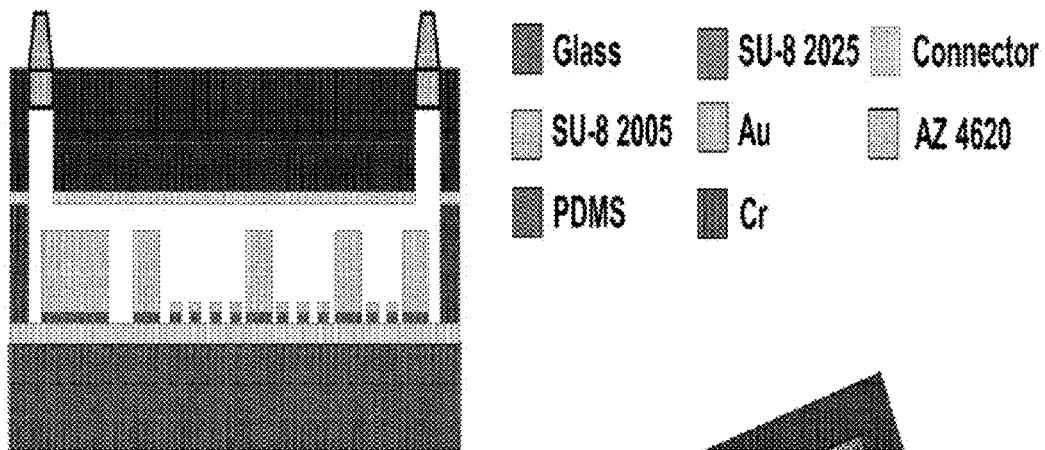
Figure 9H:
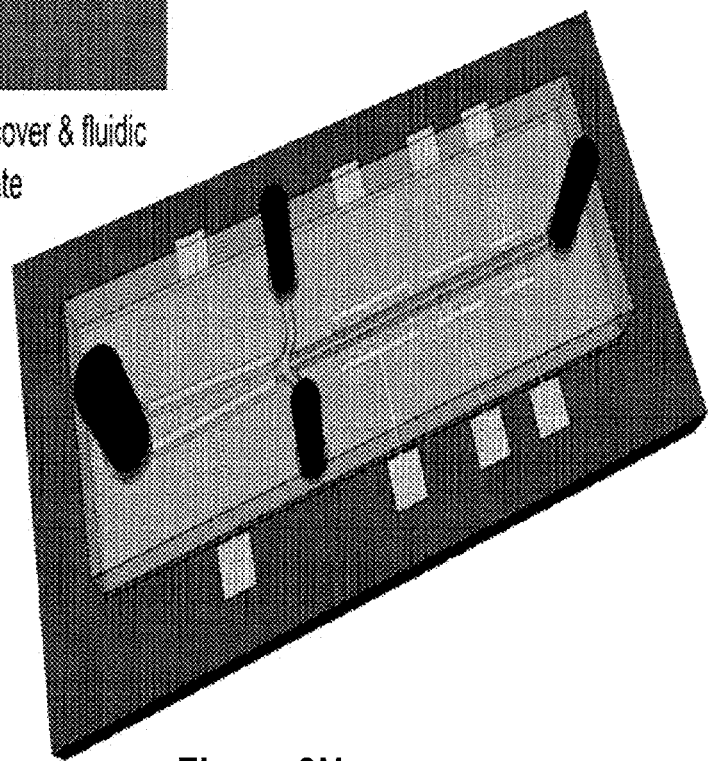

In another example embodiment, the biosensor apparatus may comprise a focusing region with the rampdown channel and rampdown electrodes followed by a detection region that includes a plurality of detection electrode arrays in series. In this example embodiment, the trapping electrode arrays may be omitted. FIGS. 9A-9H depict an example fabrication process for such a biosensor apparatus. FIG. 9A shows a step of physical vapor deposition of Cr/Au on a SU-8 2005 layer to create a sputtered thin film Au surface. FIG. 9B shows a next step of wet etching of Au to pattern the electrode structures, including the focusing electrode array and the detection electrode arrays. FIG. 9C shows a step of spincoating and patterning AZ 4620 to create a mold for Au electroplating. FIG. 9D shows a step of electroplating Au to create a vertical side wall electrode for the focusing electrode array. FIG. 9E shows a step of removing the AZ 4620 electroplating mold. FIG. 9F shows a step of wet etching of Cr to complete the patterning of the electrode structure. FIG. 9G shows a step of spincoating SU-2025 to form and pattern the microchannel layer. FIG. 9H shows a step of bonding a PDMS cover and fluidic connectors to the substrate to yield the biosensor apparatus.

While the example embodiments described above can be characterized as two-dimensional (2D) biosensors due to the electrodes being oriented along two dimensions (horizontal and vertical), it should be understood that embodiments of the inventive biosensor designs can also be 3D. For example, FIGS. 10A and 10B depict example embodiments of a three-dimensional biosensor apparatus.

Figure 10A:
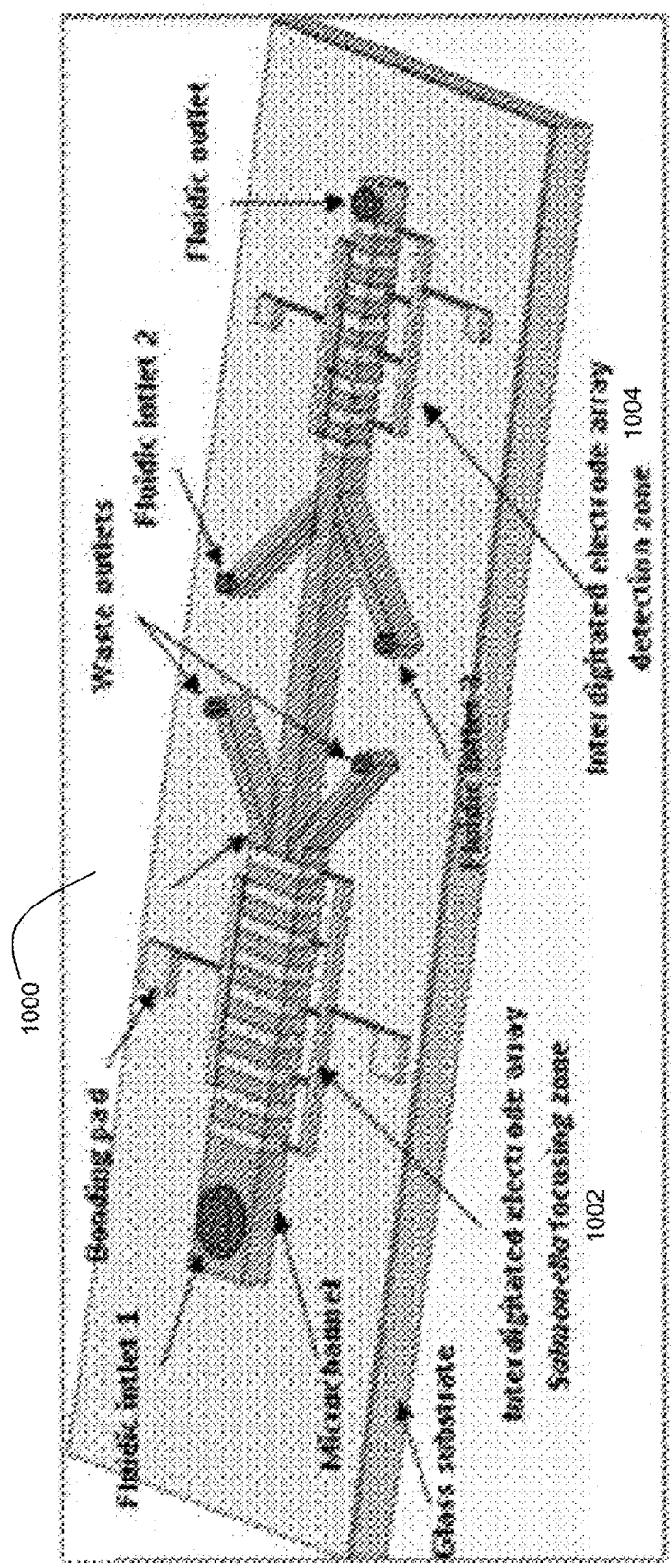
FIGS. 10A and 10B depict example embodiments of a three-dimensional biosensor apparatus.

FIG. 10A shows a biosensor apparatus 1000 that is designed to detect the presence of *Salmonella* in a sample. The focusing region/zone includes an interdigitated electrode array 1002 that fully surrounds the microchannel as shown by FIG. 10A. In this example embodiment, the focusing interdigitated electrode array 1002 employs n-DEP to concentrate the *Salmonella* toward the central region of the channel while diverting the bulk fluid to the outer region of the channel. Control over whether the electrodes generate n-DEP or p-DEP can be achieved by changing the frequency of the voltage signal applied to the electrodes. The permeability of the substance of interest and the media in which the substance resides as well as the frequency of operation affect the decision as to whether n-DEP or p-DEP should be used to direct the substance of interest in a desired manner. As n-DEP forces the *Salmonella* toward the central region of the channel where the electric field will be low, the concentrated flow of *Salmonella* proceeds along the center channel into the detection region while the bulk fluid is diverted into the outer waste outlets. The detection region/zone also includes an interdigitated electrode array 1004 that fully surrounds the microchannel as shown by FIG. 10B. A *Salmonella*-specific antibody can be introduced into the detection region via fluidic inlets in order to promote attachment of the *Salmonella* to the detection electrodes.

Figure 10B:
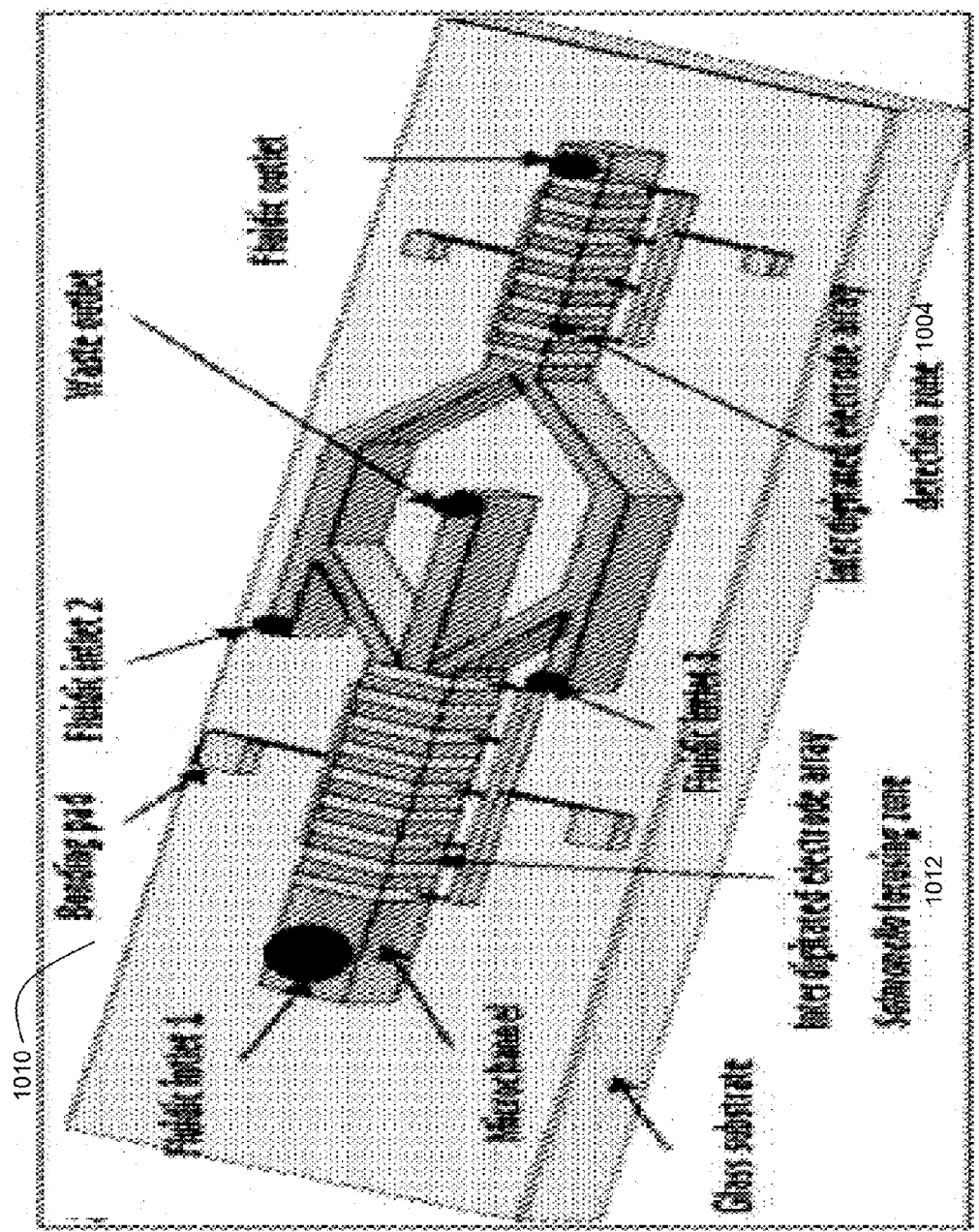

FIG. 10B shows another biosensor apparatus 1010 that is designed to detect the presence of *Salmonella* in a sample. The focusing region/zone includes an interdigitated electrode array 1012 that fully surrounds the microchannel as shown by FIG. 10B. In this example embodiment, the focusing interdigitated electrode array 1012 employs p-DEP to concentrate the *Salmonella* toward the outer region of the channel while diverting the bulk fluid to the center region of the channel. As noted above, the p-DEP can be created by changing the frequency of the voltage applied to the electrodes. The concentrated flow of *Salmonella* is diverted into the path branches from the outer region of the channel into the detection region while the bulk fluid is diverted into a central waste outlet. The detection region/zone also includes an interdigitated electrode array 1004 that fully surrounds the microchannel as shown by FIG. 10B. A *Salmonella*-specific antibody can be introduced into the detection region via fluidic inlets in order to promote attachment of the *Salmonella* to the detection electrodes.

Figure 10C:
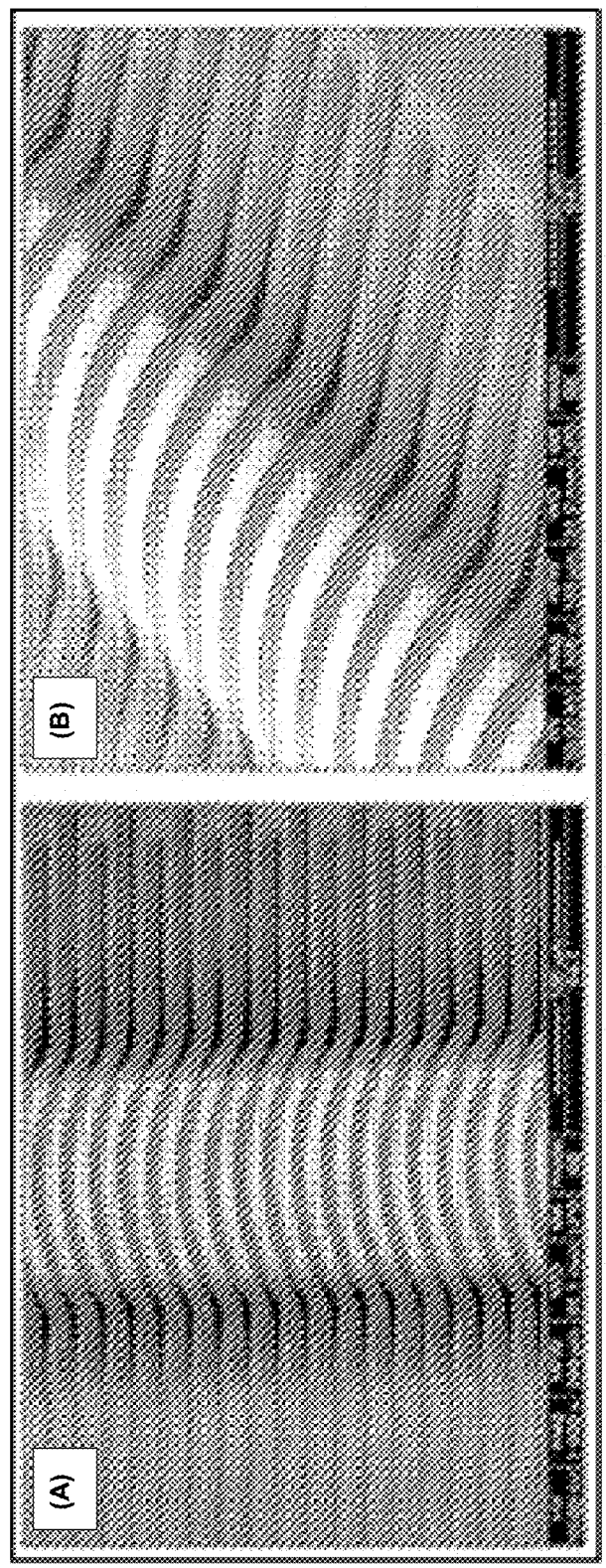
FIG. 10C depicts SEM micrographs of the electrodes in the focusing and detection regions of the apparatus examples shown by FIGS. 10A and 10B.

FIG. 10C depicts SEM micrograph views of the electrodes in the focusing and detection regions of the apparatus examples shown by FIGS. 10A and 10B, where the view of FIG. 10B is a zoomed in perspective view of the view shown by FIG. 10A.

Figure 11A:
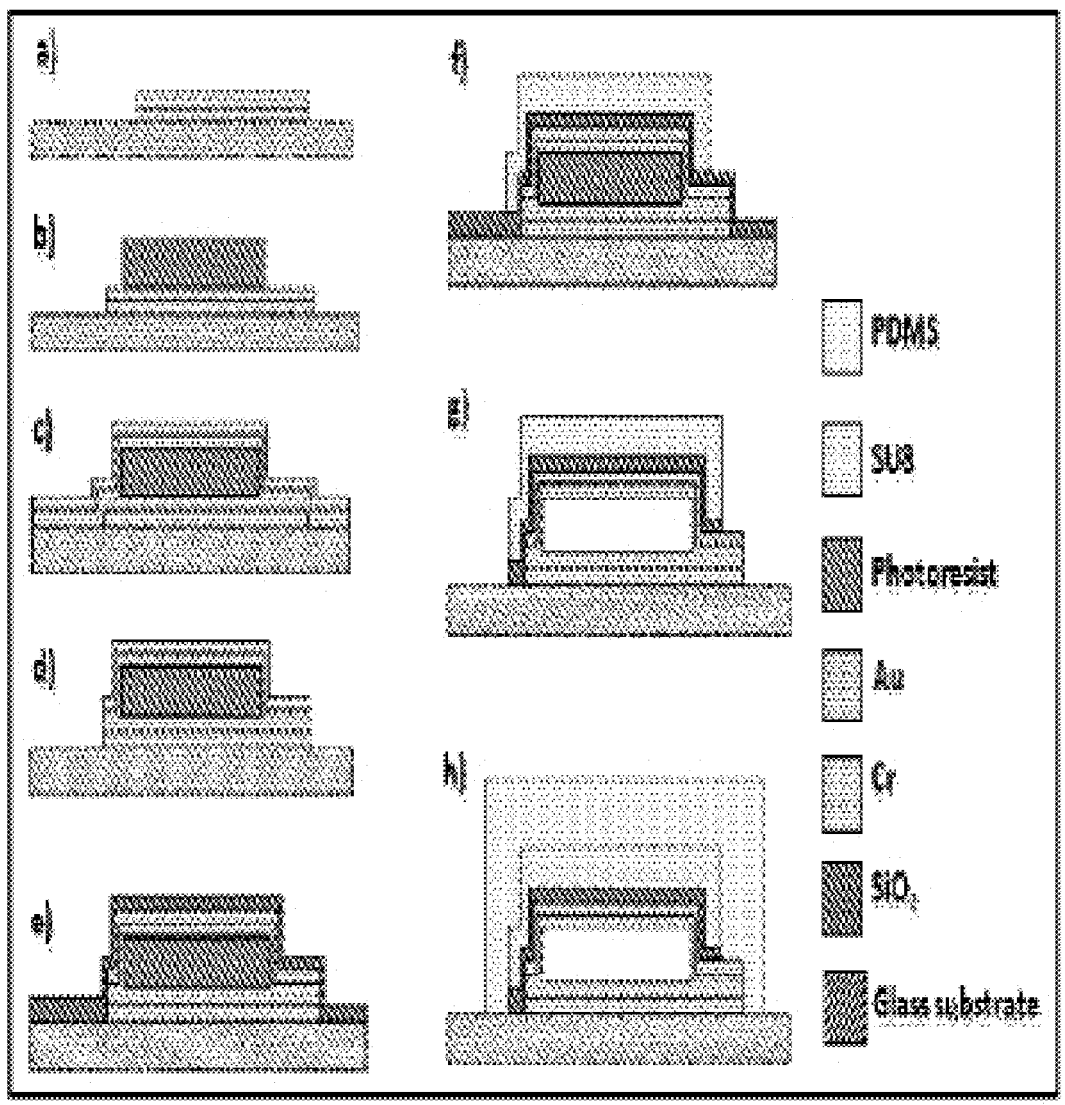
FIG. 11A depicts an example fabrication process for a biosensor apparatus in accordance with the example embodiments of FIGS. 10A and 10B.

FIG. 11A depicts an example fabrication process for a biosensor apparatus in accordance with the example embodiments of FIGS. 10A and 10B, showing the progression of device fabrication from steps (a) through (h). FIG. 11B depicts an example electrode fabrication process for a biosensor apparatus in accordance with the example embodiments of FIGS. 10A and 10B. Frame (a) of FIG. 11B shows a patterned bottom interdigitated electrode array, and frame (b) of FIG. 11B shows a patterned photoresist sacrificial microchannel across the interdigitated electrode fingers. The middle two frames of FIG. 11B show an optical image and SEM micrograph of the photoresist sacrificial channel on the interdigitated electrode array. The bottom two frames of FIG. 11B show an SEM micrograph of the patterned interdigitated electrode fingers on top of the sacrificial microchannel.

While the present invention has been described above in relation to example embodiments, various modifications may be made thereto that still fall within the invention's scope, as would be recognized by those of ordinary skill in the art. Such modifications to the invention will be recognizable upon review of the teachings herein. As such, the full scope of the present invention is to be defined solely by the appended claims and their legal equivalents.

What is claimed is:

1. An impedance-based sensor apparatus comprising:
a channel adapted to provide a path for a flow of fluid material that comprises a substance, wherein the channel includes a first channel region and a second channel region, wherein the second channel region is downstream from the first channel region with respect to the flow path for the fluid material, and wherein first channel region is arranged as a rampdown channel;
a first plurality of electrodes positioned in the first channel region, the first plurality of electrodes configured to generate a non-uniform electric field within the first channel region that produces a dielectrophoresis effect on the substance to thereby focus a flow of the fluid material into the second channel region that has a higher concentration of the substance relative to the fluid material at an inlet to the first channel region;
a second plurality of electrodes positioned in the second channel region, the second plurality of electrodes configured to exhibit a change in impedance based on a concentration of the substance in the fluid material within the second channel region; and
a third plurality of electrodes, the third plurality of electrodes configured to generate a non-uniform electric field within second channel region that produces a dielectrophoresis effect on the substance within the second channel region to trap a concentration of the substance in the second channel region for detection by the second plurality of electrodes;
wherein the third plurality of electrodes comprise a first pair of opposing electrodes upstream from the second plurality of electrodes with respect to the flow path for the fluid material and a second pair of opposing electrodes downstream from the second plurality of electrodes with respect to the flow path for the fluid material; and
wherein the first and second pairs of opposing electrodes exhibit an elliptical shape.

2. The apparatus of claim 1 wherein the first plurality of electrodes comprise an opposing pair of electrodes in a rampdown orientation that define the rampdown channel.

3. The apparatus of claim 2 wherein the first plurality of electrodes further comprise a plurality of opposing finger pair electrodes that extend outward from the opposing pair of electrodes in the rampdown orientation.

4. The apparatus of claim 3 wherein the opposing finger pair electrodes are orthogonal to the opposing pair of electrodes in the rampdown orientation.

5. The apparatus of claim 3 wherein the opposing finger pair electrodes are tilted at an angle such that the opposing finger pair electrodes are not perpendicular to a center line of a longitudinal axis for the first channel region.

6. The apparatus of claim 5 wherein the opposing finger pair electrodes include distal ends away from the opposing pair of electrodes in the rampdown orientation, and wherein the opposing finger pair electrodes are positioned in the first channel region such that there is a gap in the first channel region between the distal ends of the opposing finger pair electrodes.

7. The apparatus of claim 3 wherein the first plurality of electrodes are configured to receive an alternating voltage at a specified frequency to generate the non-uniform electric field within the first channel region and thereby produce a positive dielectrophoresis effect on the substance in the first channel region that causes a higher concentration of the substance within a central region of the first channel region than an outer region of the first channel region, wherein the second channel region is positioned to receive a flow of the fluid material from the central region of the first channel region, and wherein the first channel region includes a waste outlet in the outer region that diverts the fluid material in the outer region away from the second channel region.

8. The apparatus of claim 1 wherein the third plurality of electrodes are configured to receive an alternating voltage at a specified frequency to generate the non-uniform electric field within the second channel region and thereby produce a negative dielectrophoresis effect on the substance within the second channel region that causes a higher concentration of the substance to be positioned near the second plurality of electrodes.

9. The apparatus of claim 1 wherein the second plurality of electrodes comprise an interdigitated electrode array.

10. The apparatus of claim 1 wherein the substance comprises an antigen, and wherein the second channel region includes an inlet for introducing an antibody into the second channel region.

11. The apparatus of claim 1 wherein the third plurality of electrodes comprise a pair of opposing electrodes that sandwich the second plurality of electrodes in the second channel region such that (1) a first of the second plurality of electrodes is positioned between a first of the third plurality of electrodes and the flow path through the second channel region, and (2) a second of the second plurality of electrodes is positioned between a second of the third plurality of electrodes and the flow path through the second channel region.

12. The apparatus of claim 11 wherein the first plurality of electrodes comprise an opposing pair of electrodes in a rampdown orientation that define the rampdown channel.

13. The apparatus of claim 12 wherein the first plurality of electrodes further comprise a plurality of opposing finger pair electrodes that extend outward from the opposing pair of electrodes in the rampdown orientation.

14. The apparatus of claim 1 wherein the second channel region comprises a plurality of detection regions, each detection region including its own subset of the second plurality of electrodes.

15. The apparatus of claim 14 wherein a plurality of the detection regions are arranged in series.

16. The apparatus of claim 14 wherein a plurality of the detection regions are arranged in parallel.

17. The apparatus of claim 14 wherein the detection regions are adapted for selective pressurization of the detection regions.

18. The apparatus of claim 14 wherein the third plurality of electrodes comprise a plurality of pairs of opposing electrodes that separate the detection regions.

19. The apparatus of claim 14 wherein the substance comprises an antigen, and wherein each detection region includes an inlet for introducing an antibody into that detection region.

20. The apparatus of claim 19 wherein a plurality of the detection regions are arranged for parallel detection of a plurality of different substances without cross-contamination.

21. The apparatus of claim 19 wherein the detection regions are arranged for parallel detection of a plurality of different antigens without cross-contamination.

22. The apparatus of claim 14 wherein the channel is angled such that a plurality of the detection regions are not aligned along a common axis.

23. The apparatus of claim 1 wherein the first channel region comprises a plurality of focusing regions, each focusing region including its own subset of the first plurality of electrodes, wherein each subset of the first plurality of electrodes comprises an opposing pair of electrodes in a rampdown orientation to define a rampdown channel within its focusing region.

24. The apparatus of claim 23 wherein a plurality of the focusing regions are arranged in series.

25. The apparatus of claim 23 wherein a plurality of the focusing regions are arranged in parallel.

26. The apparatus of claim 1 further comprising:
an antibody that promotes attachment of the substance to the second plurality of electrodes.

27. The apparatus of claim 26 wherein the antibody is resident in the second channel region.

28. The apparatus of claim 26 wherein the antibody promotes attachment of bacteria to the second plurality of electrodes, and wherein the bacteria serves as the substance.

29. The apparatus of claim 28 wherein the antibody promotes attachment of bacteria of the family Enterobacteriaceae to the second plurality of electrodes.

30. The apparatus of claim 29 wherein the antibody promotes attachment of bacteria of the family Enterobacteriaceae selected from the group consisting of *Escherichia, Klebsiella, Proteus, Enterobacter, Aerobacter, Serratia, Providencia, Citrobacter, Morganella, Yersinia, Envinia, Shigella, Salmonella*, and combinations thereof to the second plurality of electrodes.

31. The apparatus of claim 28 wherein the antibody promotes attachment of bacteria that comprise at least one of *Bacillus, Campylobacter, Listeria, Staphylococcus, Streptococcus*, and *Vibrio* to the second plurality of electrodes.

32. The apparatus of claim 1 wherein the channel is arranged as a microchannel; and
wherein the microchannel, the first plurality of electrodes, the second plurality of electrodes, and the third plurality of electrodes are resident on a single substrate.

33. The apparatus of claim 32 wherein the substrate has a planar dimension that defines a floor for the microchannel;
wherein the first plurality of electrodes comprise an opposing pair of electrodes in a rampdown orientation that define the rampdown channel; and
wherein the opposing pair of electrodes in the rampdown orientation are vertical relative to the floor.

34. The apparatus of claim 33 wherein the first plurality of electrodes further comprise a plurality of opposing finger pair electrodes that extend outward from the opposing pair of electrodes in the rampdown orientation.

35. The apparatus of claim 32 wherein the substrate has a planar dimension that defines a floor for the microchannel; and
wherein the third plurality of electrodes are vertical relative to the floor.

36. The apparatus of claim 1 wherein the second plurality of electrodes are washable for reusability of the apparatus.

37. An impedance-based sensor apparatus comprising:
a channel adapted to provide a path for a flow of fluid material that comprises a substance, wherein the channel includes a first channel region and a second channel region, wherein the second channel region is downstream from the first channel region with respect to the flow path for the fluid material, and wherein first channel region is arranged as a rampdown channel;
a first plurality of electrodes positioned in the first channel region, the first plurality of electrodes configured to generate a non-uniform electric field within the first channel region that produces a dielectrophoresis effect on the substance to thereby focus a flow of the fluid material into the second channel region that has a higher concentration of the substance relative to the fluid material at an inlet to the first channel region;
a second plurality of electrodes positioned in the second channel region, the second plurality of electrodes configured to exhibit a change in impedance based on a concentration of the substance in the fluid material within the second channel region; and
a third plurality of electrodes, the third plurality of electrodes configured to generate a non-uniform electric field within second channel region that produces a dielectrophoresis effect on the substance within the second channel region to trap a concentration of the substance in the second channel region for detection by the second plurality of electrodes;
wherein the third plurality of electrodes comprise a first pair of opposing electrodes upstream from the second plurality of electrodes with respect to the flow path for the fluid material and a second pair of opposing electrodes downstream from the second plurality of electrodes with respect to the flow path for the fluid material; and wherein the first and second pairs of opposing electrodes lie in different planes that are not parallel with each other.

38. The apparatus of claim 37 wherein the first and second pairs of opposing electrodes are orthogonal to the second plurality of electrodes.

* * * * *